US011668772B2

(12) United States Patent
Kataoka

(10) Patent No.: US 11,668,772 B2
(45) Date of Patent: Jun. 6, 2023

(54) MAGNETIC FIELD MEASUREMENT DEVICE, MAGNETIC FIELD MEASUREMENT METHOD, AND RECORDING MEDIUM HAVING RECORDED THEREON MAGNETIC FIELD MEASUREMENT PROGRAM

(71) Applicant: Asahi Kasei Microdevices Corporation, Tokyo (JP)

(72) Inventor: Makoto Kataoka, Tokyo (JP)

(73) Assignee: Asahi Kasei Microdevices Corporation, Tokyo (JP)

( * ) Notice: Subject to any disclaimer, the term of this patent is extended or adjusted under 35 U.S.C. 154(b) by 0 days.

(21) Appl. No.: 17/579,366

(22) Filed: Jan. 19, 2022

(65) Prior Publication Data
US 2022/0229125 A1 Jul. 21, 2022

(30) Foreign Application Priority Data
Jan. 20, 2021 (JP) .............................. JP2021-007508

(51) Int. Cl.
*G01R 33/09* (2006.01)
*G01R 33/00* (2006.01)

(52) U.S. Cl.
CPC ........ *G01R 33/093* (2013.01); *G01R 33/0011* (2013.01); *G01R 33/0035* (2013.01); *G01R 33/098* (2013.01)

(58) Field of Classification Search
CPC combination set(s) only.
See application file for complete search history.

(56) References Cited

U.S. PATENT DOCUMENTS 11,454,679 B2   9/2022   Okatake
2004/0207396 A1  10/2004  Xiao
(Continued)

FOREIGN PATENT DOCUMENTS

JP   2005049179 A   2/2005
JP   2006047080 A   2/2006
(Continued)

OTHER PUBLICATIONS

Kensuke Sekihara,"Signal Space Separation Method for a Biomagnetic Sensor Array Arranged on a Flat Plane for Magnetocardiographic Applications: A Computer Simulation Study",Hindawi Journal of Healthcare Engineering,vol. 2018, Article ID 7689589, 19 pages,https://doi.org/10.1155/2018/7689589, pp. 1-19.
(Continued)

*Primary Examiner* — Alvaro E Fortich

(57) ABSTRACT

There is provide a magnetic field measurement device including: a magnetic sensor array configured by a plurality of magnetic sensor cells, each of which has a magnetic sensor; a magnetic field acquisition section configured to acquire measurement data measured by the magnetic sensor array; a signal space separation section configured to perform signal separation to separate, into internal space data and external space data, a spatial distribution of a magnetic field which is indicated by the measurement data, based on a position and a magnetic sensitivity of each magnetic sensor; and a calculation processing section configured to remove, from the internal space data, at least a part of a variation component common to magnetic field measurement data that indicates the spatial distribution of the magnetic field which is indicated by the measurement data, and the external space data.

20 Claims, 17 Drawing Sheets

(56) References Cited

U.S. PATENT DOCUMENTS

| | | |
|---|---|---|
| 2006/0031038 A1* | 2/2006 | Simola .................. G01R 33/02 |
| | | 702/127 |
| 2007/0108962 A1 | 5/2007 | Taulu |
| 2008/0161714 A1 | 7/2008 | Ahonen |
| 2009/0069661 A1 | 3/2009 | Taulu |
| 2009/0184709 A1 | 7/2009 | Kajola |
| 2013/0109954 A1 | 5/2013 | Simola |
| 2013/0214774 A1 | 8/2013 | Cesaretti |
| 2014/0343882 A1 | 11/2014 | Taulu |
| 2017/0212188 A1 | 7/2017 | Kikitsu |
| 2017/0248665 A1* | 8/2017 | Ludwig .............. G01R 33/3415 |
| 2017/0299662 A1* | 10/2017 | Nagasaka ............ G01R 33/035 |
| 2017/0352800 A1 | 12/2017 | Racz |
| 2018/0014738 A1 | 1/2018 | Tanaka |
| 2018/0275215 A1 | 9/2018 | Uchida |
| 2018/0340987 A1 | 11/2018 | Latham |
| 2019/0004122 A1 | 1/2019 | Jung |
| 2019/0125268 A1 | 5/2019 | Taulu |
| 2019/0133478 A1* | 5/2019 | Varcoe .................. A61B 5/245 |
| 2019/0298202 A1 | 10/2019 | Nakamura |
| 2021/0161420 A1 | 6/2021 | Nakamura |

FOREIGN PATENT DOCUMENTS

| | | |
|---|---|---|
| JP | 2012152514 A | 8/2012 |
| JP | 2017133933 A | 8/2017 |
| JP | 2018054461 A | 4/2018 |
| JP | 2020148760 A | 9/2020 |
| WO | 03046587 A1 | 6/2003 |
| WO | 2006114473 A1 | 11/2006 |

OTHER PUBLICATIONS

Samu Taula et al.,"Presentation of electromagnetic multichannel data: The signal space separation method", Journal of Applied Physics 97, 124905 (2005),pp. 124905-1-124905-10.

Samu Taulu et al., "Applications of the Signal Space Separation Method",IEEE Transactions on Signal Processing, vol. 53, No. 9, Sep. 2005,pp. 3359-3372.

F Chella et al.,"Calibration of a multichannel MEG system based on the Signal Space Separation method" Physics in Medicine and Biology: 57 (2012) 4855-4870.

\* cited by examiner

MAGNETIC FIELD MEASUREMENT DEVICE, MAGNETIC FIELD MEASUREMENT METHOD, AND RECORDING MEDIUM HAVING RECORDED THEREON MAGNETIC FIELD MEASUREMENT PROGRAM

The contents of the following Japanese patent application(s) are incorporated herein by reference:
NO. 2021-007508 filed in JP on Jan. 20, 2021

BACKGROUND

1. Technical Field

The present invention relates to a magnetic field measurement device, a magnetic field measurement method, and a recording medium having recorded thereon a magnetic field measurement program.

2. Related Art

Patent Document 1 discloses that "for example, SSP operation is used to eliminate interference in an intermediate space".

CITATION LIST

Patent Document

[Patent Document 1] International Publication No. 2006/114473

SUMMARY

A first aspect of the present invention provides a magnetic field measurement device. The magnetic field measurement device may include a magnetic sensor array configured by a plurality of magnetic sensor cells, each of which has a magnetic sensor. The magnetic field measurement device may include a magnetic field acquisition section configured to acquire measurement data measured by the magnetic sensor array. The magnetic field measurement device may include a signal space separation section configured to perform signal separation to separate, into internal space data and external space data, a spatial distribution of a magnetic field which is indicated by the measurement data, based on a position and a magnetic sensitivity of each magnetic sensor. The magnetic field measurement device may include a calculation processing section configured to remove, from the internal space data, at least a part of a variation component common to magnetic field measurement data that indicates the spatial distribution of the magnetic field which is indicated by the measurement data, and the external space data.

The calculation processing section may be configured to extract the common variation component based on a correlation between a basis of a time domain in the magnetic field measurement data, and a basis of a time domain in the external space data.

The calculation processing section may be configured to respectively calculate the basis of the time domain in the magnetic field measurement data and the basis of the time domain in the external space data, by respectively performing singular value decomposition on the magnetic field measurement data and the external space data.

The calculation processing section may be configured to extract the common variation component by performing principal component analysis on the basis of the time domain in the magnetic field measurement data and the basis of the time domain in the external space data.

The calculation processing section may be configured to calculate a coefficient of the correlation by performing the singular value decomposition on a covariance of the basis of the time domain in the magnetic field measurement data and the basis of the time domain in the external space data, and extract, as the common variation component, a component of which the coefficient of the correlation exceeds a predetermined threshold value.

The magnetic sensor may include a magnetic resistance element.

The magnetic sensor may further include magnetic flux concentrators that are respectively arranged at both of one end and the other end of the magnetic resistance element.

Each of the plurality of magnetic sensor cells may further include a magnetic field generation section configured to generate a feedback magnetic field to reduce an input magnetic field detected by the magnetic sensor, and an output section configured to output an output signal in accordance with a feedback current which is caused to flow for the magnetic field generation section to generate the feedback magnetic field.

The signal space separation section may be configured to perform the signal separation on the spatial distribution of the magnetic field, based on basis vectors calculated from orthonormal functions, and the position and the magnetic sensitivity.

The signal space separation section may be configured to perform the signal separation on the spatial distribution of the magnetic field, through series expansion of the basis vectors.

The signal space separation section may be configured to calculate expansion coefficients of the basis vectors by a method of least squares.

The orthonormal functions may be expressed with spherical harmonics.

The magnetic field measurement device may further include a calibration calculation section configured to calibrate the measurement data acquired by the magnetic field acquisition section.

The magnetic sensor array may be configured by the plurality of magnetic sensor cells being arrayed to form a surface covering at least a part of a measurement target.

In the magnetic sensor array, the plurality of magnetic sensor cells may be three-dimensionally arrayed to be arranged at grid points between two curved surfaces curved in one direction.

The curved surfaces may be formed to be substantially parabolic.

The calculation processing section may be configured to remove, from the internal space data, at least a part of a variation component common to data obtained by subtracting the internal space data from the magnetic field measurement data, and the external space data.

A second aspect of the present invention provides a magnetic field measurement method. The magnetic field measurement method may include acquiring measurement data measured by a magnetic sensor array configured by a plurality of magnetic sensor cells, each of which has a magnetic sensor. The magnetic field measurement method may include performing signal separation to separate, into internal space data and external space data, a spatial distribution of a magnetic field which is indicated by the measurement data, based on a position and a magnetic sensitivity of each magnetic sensor. The magnetic field measurement method may include removing, from the internal space data, at least a part of a variation component common to magnetic field measurement data that indicates the spatial distribution of the magnetic field which is indicated by the measurement data, and the external space data.

A third aspect of the present invention provides a recording medium having recorded thereon a magnetic field measurement program. The magnetic field measurement program may be executed by a computer. The magnetic field measurement program may cause the computer to function as a magnetic field acquisition section configured to acquire measurement data measured by a magnetic sensor array configured by a plurality of magnetic sensor cells, each of which has a magnetic sensor. The magnetic field measurement program may cause the computer to function as a signal space separation section configured to perform signal separation to separate, into internal space data and external space data, a spatial distribution of a magnetic field which is indicated by the measurement data, based on a position and a magnetic sensitivity of each magnetic sensor. The magnetic field measurement program may cause the computer to function as a calculation processing section configured to remove, from the internal space data, at least a part of a variation component common to magnetic field measurement data that indicates the spatial distribution of the magnetic field which is indicated by the measurement data, and the external space data.

The summary clause does not necessarily describe all necessary features of the embodiments of the present invention. The present invention may also be a sub-combination of the features described above.

DESCRIPTION OF EXEMPLARY EMBODIMENTS

Hereinafter, the invention will be described through embodiments of the invention, but the following embodiments do not limit the invention according to claims. In addition, not all of the combinations of features described in the embodiments are essential for means to solve the problem in the invention.

Figure 1:
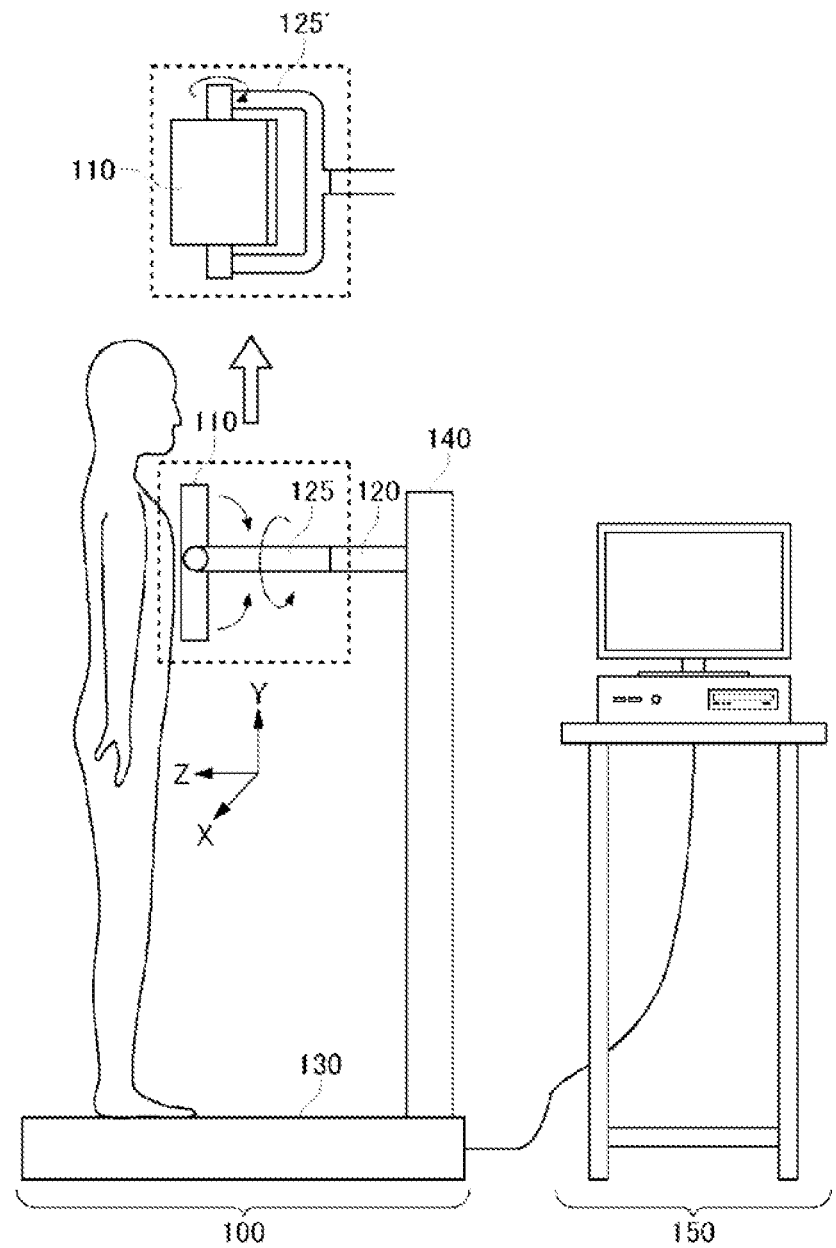
FIG. 1 shows a configuration of a magnetic field measurement device 10 according to the present embodiment.

FIG. 1 shows a configuration of a magnetic field measurement device 10 according to the present embodiment. The magnetic field measurement device 10 according to the present embodiment performs a signal separation to separate, into internal space data and external space data, a spatial distribution of a magnetic field which is indicated by magnetic field measurement data measured by using a magnetic sensor array. Further, the magnetic field measurement device 10 removes, from the internal space data, at least a part of a variation component common to the magnetic field measurement data and the external space data. As one example in the present embodiment, a case where the magnetic field measurement device 10 is a magnetocardiographic measurement device that measures a cardiac magnetic field which is a magnetic field generated by an electrical activity of a human heart, is described. However, the present invention is not limited to this. The magnetic field measurement device 10 may be used for measuring a cardiac magnetic field of a living subject other than a human, or may be used for measuring a biomagnetic field, such as a brain magnetic field, other than the cardiac magnetic field. In addition, the magnetic field measurement device 10 may be used for magnetic particle testing for detecting flaws and the like of a surface and a subsurface of iron and steel materials and welded parts.

The magnetic field measurement device 10 includes a main body section 100 and an information processing section 150. The main body section 100 is a component for sensing the cardiac magnetic field of a subject, and has a magnetic sensor unit 110, a head 120, a drive section 125, a base section 130, and a pole section 140.

The magnetic sensor unit 110 is arranged at a position toward a heart in a chest of the subject during a magnetocardiographic measurement, and senses the cardiac magnetic field of the subject. The head 120 supports the magnetic sensor unit 110, and causes the magnetic sensor unit 110 to face the subject. The drive section 125 is provided between the magnetic sensor unit 110 and the head 120, and changes an orientation of the magnetic sensor unit 110 relative to the head 120 when calibration is performed. The drive section 125 according to the present embodiment includes a first actuator that can cause the magnetic sensor unit 110 to rotate 360 degrees about a Z axis in the drawing, and a second actuator that causes the magnetic sensor unit 110 to rotate about an axis perpendicular to the Z axis (an X axis for a state in the drawing), and changes an azimuth angle and a zenith angle of the magnetic sensor unit 110 by using these actuators. As shown by the drive section 125 in the drawing, the drive section 125 has a Y shape when viewed from a Y axis direction in the drawing, and the second actuator can cause the magnetic sensor unit 110 to rotate 360 degrees about the X axis in the drawing.

The base section 130 is a base that supports other parts, and is a base on which the subject stands during the magnetocardiographic measurement in the present embodiment. The pole section 140 supports the head 120 at the height of the chest of the subject. The pole section 140 may be capable of extending and contracting in an up and down direction to adjust the height of the magnetic sensor unit 110 to the height of the chest of the subject.

The information processing section 150 is a component for processing measurement data which is obtained by the main body section 100 and outputting the processed measurement data through printing, displaying, or the like. The information processing section 150 may be a computer such as a PC (a personal computer), a tablet type computer, a smartphone, a workstation, a server computer, or a general-purpose computer, or may be a computer system in which a plurality of computers are connected. Alternatively, the information processing section 150 may be a dedicated computer designed for information processing of the magnetocardiographic measurement, or may be dedicated hardware realized by dedicated circuitry.

Figure 2:
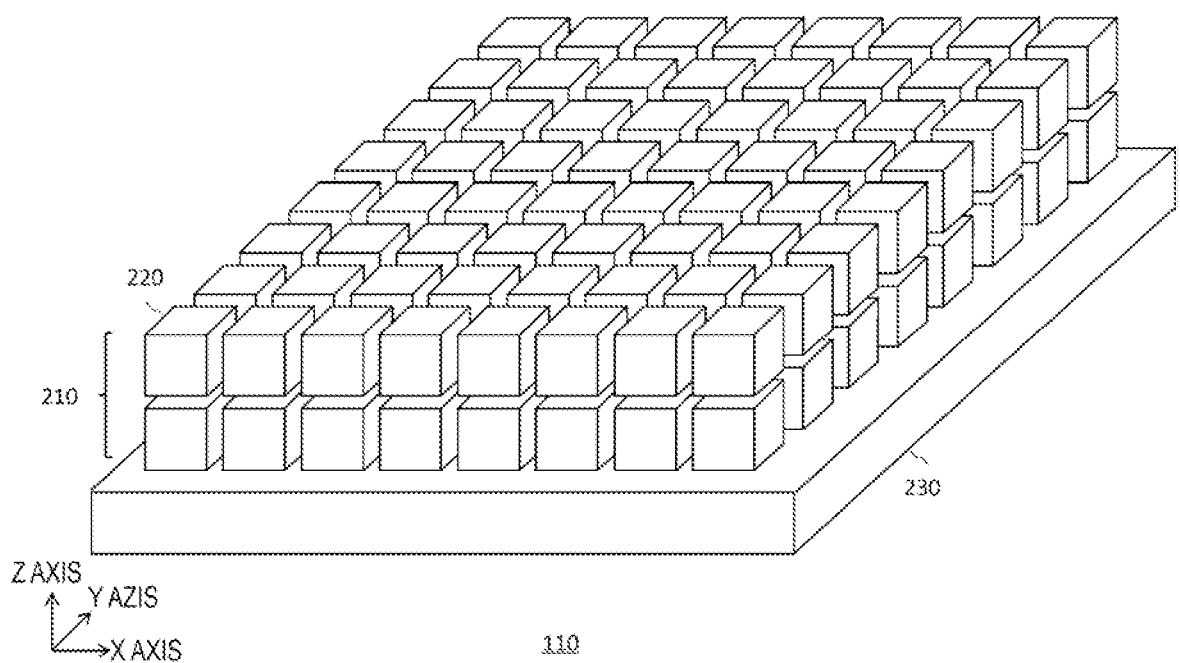
FIG. 2 shows a configuration of a magnetic sensor unit 110 according to the present embodiment.

FIG. 2 shows a configuration of a magnetic sensor unit 110 according to the present embodiment. The magnetic sensor unit 110 includes a magnetic sensor array 210 and a sensor data collection section 230. The magnetic sensor array 210 has a plurality of magnetic sensor cells 220, and is capable of detecting an input magnetic field in three axial directions. The present drawing shows a case where the magnetic sensor array 210 has the plurality of magnetic sensor cells 220 arranged in each of an X direction, a Y direction, and a Z direction (for example, a total of 128 magnetic sensor cells 220 with 8 cells arranged in the X direction, 8 cells arranged in the Y direction, and 2 cells arranged in the Z direction).

The sensor data collection section 230 is electrically connected (not illustrated) to the plurality of magnetic sensor cells 220 that are included in the magnetic sensor array 210, and collects sensor data (a detection signal) from the plurality of magnetic sensor cells 220 to supply the collected sensor data to the information processing section 150.

Figure 3:
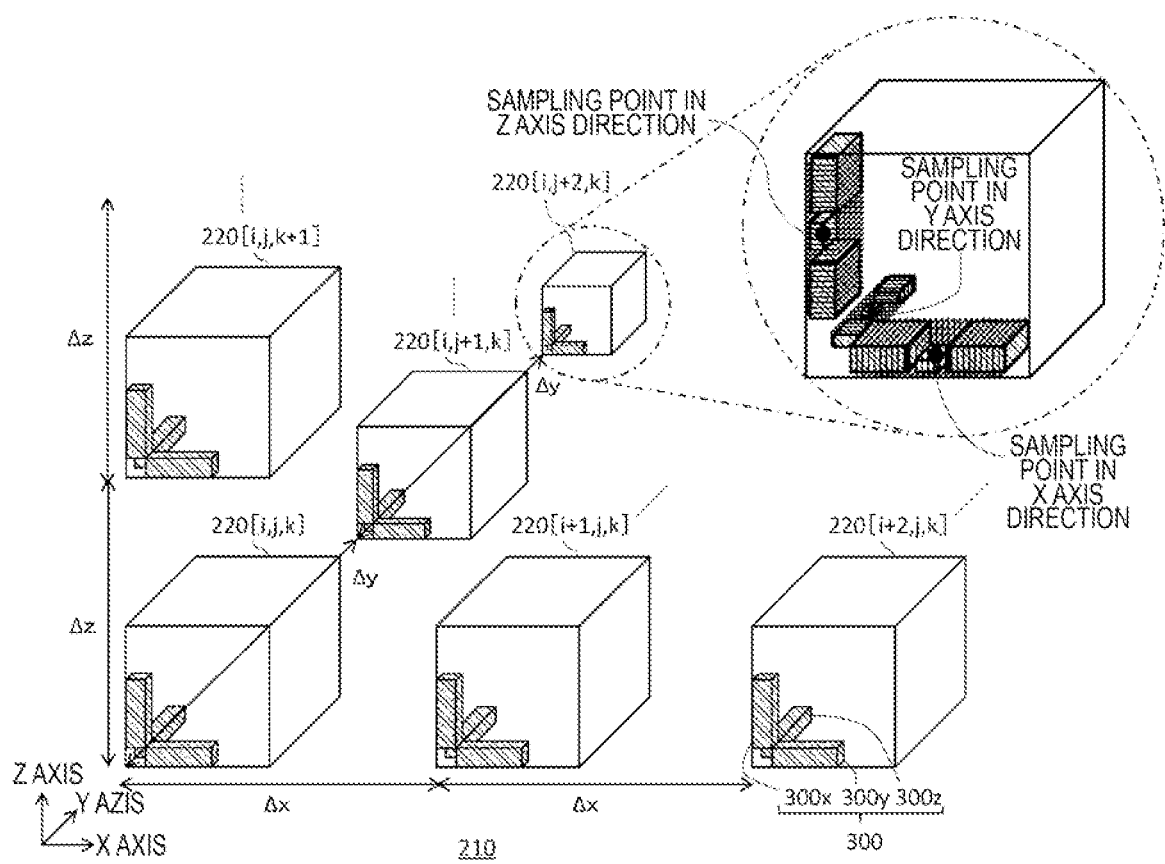
FIG. 3 shows a configuration and an arrangement of a magnetic sensor cell 220 in a magnetic sensor array 210 according to the present embodiment.

FIG. 3 shows a configuration of a magnetic sensor cell 220 in a magnetic sensor array 210 according to the present embodiment. Each of the plurality of magnetic sensor cells 220 has at least one sensor section 300, each of which has a magnetic resistance element. The present drawing shows, as one example, a case where each of the plurality of magnetic sensor cells 220 has three sensor sections 300x to z (collectively referred to as the "sensor section 300"), and is capable of detecting the input magnetic field in the three axial directions. However, all of the plurality of magnetic sensor cells 220 are not limited to having three sensor sections 300x to z, and at least a part of the magnetic sensor array 210 only needs to be capable of detecting the input magnetic field in the three axial directions. In this case, as will be described below, in a case where the magnetic sensor array 210 performs spatial sampling on spherical harmonics respectively, it is necessary to detect a dependence on a spatial frequency relating to angular momentum in the magnetic field. Therefore, an arrangement position of each sensor section 300 in the magnetic sensor array 210 may be arranged as evenly as possible at least in an azimuth angle direction and a zenith angle direction. For a similar reason, a magnetosensitive axis of each sensor in the magnetic sensor array 210 may also be arranged as evenly as possible at least in the azimuth angle direction and the zenith angle direction. The sensor section 300x is arranged along an X axis direction and is capable of detecting the magnetic field in the X axis direction. In addition, the sensor section 300y is arranged along the Y axis direction and is capable of detecting the magnetic field in the Y axis direction. In addition, the sensor section 300z is arranged along a Z axis direction and is capable of detecting the magnetic field in the Z axis direction. As shown in an enlarged view shown by the dashed and dotted line of the present drawing, in the present embodiment, each sensor section 300 has magnetic flux concentrators arranged at both ends of the magnetic resistance element. Accordingly, by using the magnetic resistance element arranged in a narrow position interposed between the magnetic flux concentrators to perform sampling on the spatial distribution of the magnetic field, it is possible for each sensor section 300 to clarify spatial sampling points in each axis direction. The details of the configuration of each sensor section 300 are described below.

The plurality of magnetic sensor cells 220 are arrayed at regular intervals $\Delta x$, $\Delta y$, and $\Delta z$, respectively along the X axis direction, the Y axis direction, and the Z axis direction. The position of each magnetic sensor cell 220 in the magnetic sensor array 210 is expressed by a set [i, j, k] of a position i in the X direction, a position j in the Y direction, and a position k in the Z direction. Here, i is an integer satisfying $1 \leq i \leq Nx$ (Nx represents the number of the arrayed magnetic sensor cells 220, which are arranged in the X direction), j is an integer satisfying $1 \leq j \leq Ny$ (Ny represents the number of the arrayed magnetic sensor cells 220, which are arranged in the Y direction), and k is an integer satisfying $1 \leq k \leq Nz$ (Nz represents the number of the arrayed magnetic sensor cells 220, which are arranged in the Z direction). It should be noted that as one example in the above description, the case where the plurality of magnetic sensor cells 220 are arrayed at regular intervals along each axial direction is shown. However, the present invention is not limited to this. The plurality of magnetic sensor cells 220 may be arrayed at different intervals from each other, for example, in at least one axis direction of any of the X axis direction, the Y axis direction, and the Z axis direction.

In the present drawing, the three axial directions of the magnetic field detected by the sensor sections 300x, 300y, and 300z are the same directions as directions of three dimensions in which the magnetic sensor cells 220 are arrayed. This makes it easy to grasp each component of the distribution of the measured magnetic field. In addition, the sensor sections 300x, 300y, and 300z are arranged in each magnetic sensor cell 220 so as not to overlap each other when viewed from each of the three-dimensional directions in which the magnetic sensor cells 220 are arrayed. In addition, in the present drawing, the sensor sections 300x, 300y, and 300z are arranged to extend in each axial direction of the three axial directions such that each sensor section has one end which is provided on a side of a gap provided between the plurality of sensor sections 300 and the other end which is provided to be away from the gap. As one example, the present drawing shows an example in which an air space (a gap) is formed at a lower left corner portion in front view of the magnetic sensor cell 220, and the sensor sections 300x, 300y, and 300z are arranged to extend in each axis direction of the X axis, Y axis, and Z axis directions such that one end of each sensor section is in contact with the air space and the other end is away from the air space. In the present drawing, the sensor sections 300x, 300y, and 300z are arranged along three sides perpendicular to each other from one corner portion of the magnetic sensor cell 220 having a cubic shape, and the air space is provided at the one corner portion. In addition, it is preferable that coils or magnetic materials, which are included in the sensor sections 300x, 300y, and 300z, and are described below, are arranged not to overlap each other. This makes it possible to clarify a measurement point, and thus it is easier to grasp each component of the measured magnetic field. In addition, cross-axis sensitivities of the sensor sections 300x, 300y, and 300z can be regarded as being equivalent to each other. These cross-axis sensitivities are caused by mutual interference between the coils or the magnetic materials of the sensor sections 300x, 300y, and 300z. However, the three axial directions in which the magnetic field is detected may be different from the three-dimensional directions in which the magnetic sensor cells 220 are arrayed. When both are different from each other, no restriction is imposed on the arrangement of the sensor sections 300 in the magnetic sensor cells 220 and an array direction of the magnetic sensor cells 220, and it is possible to increase a degree of freedom in designing the magnetic sensor array 210.

Figure 4:
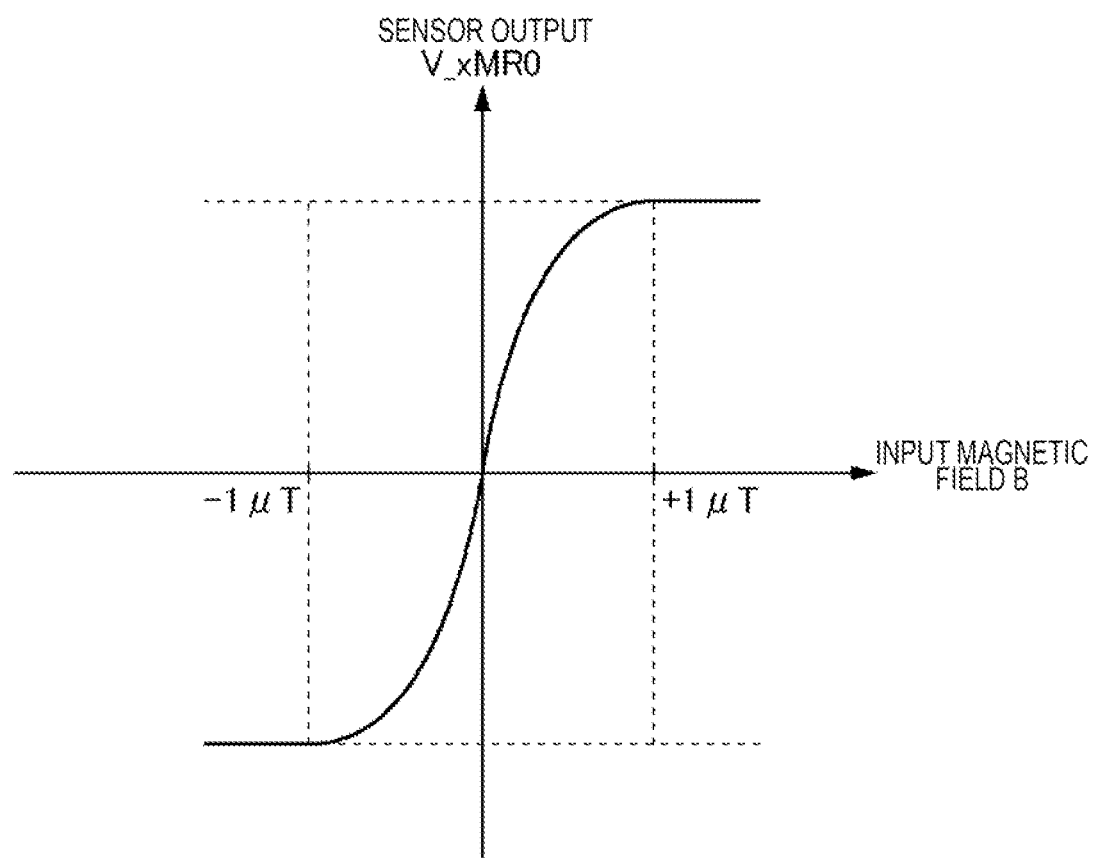
FIG. 4 shows one example of an input and output characteristic of a magnetic sensor having a magnetic resistance element according to the present embodiment.

FIG. 4 shows one example of an input and output characteristic of a magnetic sensor having a magnetic resistance element according to the present embodiment. In the present drawing, the horizontal axis represents a magnitude B of an input magnetic field which is input to the magnetic sensor, and the vertical axis represents a magnitude V_xMR0 of a detection signal of the magnetic sensor. For example, the magnetic sensor includes a giant magneto-resistance (GMR: Giant Magneto-Resistance) element, a tunnel magneto-resistance (TMR: Tunnel Magneto-Resistance) element, or the like, and detects the magnitude of the magnetic field in one predetermined axial direction.

Such a magnetic sensor has a high magnetic sensitivity, which is a slope of the detection signal V_xMR0 relative to the input magnetic field B, and can detect a very small magnetic field of approximately 10 pT. On the other hand, for example, the detection signal V_xMR0 is saturated when an absolute value of the input magnetic field B is approximately 1 µT, and the magnetic sensor has a narrow range in which linearity of the input and output characteristic is good. Thus, adding a closed loop, which generates a feedback magnetic field to such a magnetic sensor, can improve the linearity (or referred to as the linearity) of the magnetic sensor. Such a magnetic sensor is described below.

Figure 5:
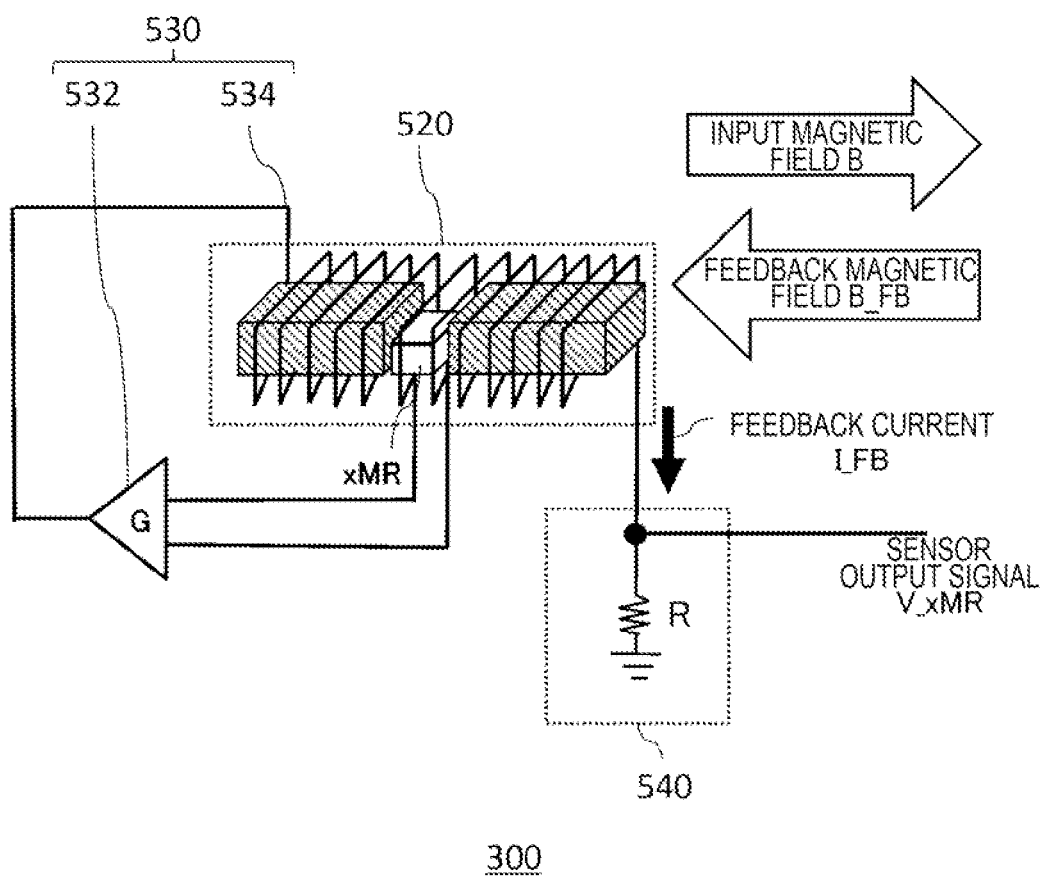
FIG. 5 shows a configuration example of a sensor section 300 according to the present embodiment.

FIG. 5 shows a configuration example of a sensor section 300 according to the present embodiment. The sensor section 300 is provided inside each of the plurality of magnetic sensor cells 220, and has a magnetic sensor 520, a magnetic field generation section 530, and an output section 540. it should be noted that parts of the sensor section 300, for example, an amplifier circuit 532 and the output section 540 may be provided on a sensor data collection section 230 side rather than on a magnetic sensor cell 220 side.

The magnetic sensor 520 has the magnetic resistance element such as the GMR element or the TMR element, similarly to the magnetic sensor described in FIG. 4. In addition, the magnetic sensor 520 has the magnetic flux concentrators arranged at both ends of the magnetic resistance element. The magnetic resistance element of the magnetic sensor 520 may be formed such that in a case where a positive direction of the magnetosensitive axis is defined as a +X direction, a resistance value increases when a magnetic field in the +X direction is input, and the resistance value decreases when the magnetic field in a −X direction is input. That is, observing a change in the resistance value of the magnetic resistance element of the magnetic sensor 520 makes it possible to detect the magnitude of the magnetic field B which is input to the magnetic sensor 520. For example, when the magnetic sensitivity of the magnetic sensor 520 is S, a detection result of the magnetic sensor 520 for the input magnetic field B can be calculated as S×B. It should be noted that as one example, the magnetic sensor 520 is connected to a power source or the like, and outputs a voltage drop in accordance with a change in resistance value, as a detection result for the input magnetic field. The details of the configuration of the magnetic sensor 520 are described below.

The magnetic field generation section 530 provides, to the magnetic sensor 520, the feedback magnetic field to reduce the input magnetic field detected by the magnetic sensor 520. For example, the magnetic field generation section 530 operates to generate a feedback magnetic field B_FB, and to cancel out the input magnetic field, the feedback magnetic field B_FB having an orientation that is the opposite of the orientation of the magnetic field B which is input to the magnetic sensor 520, and an absolute value which is substantially the same as that of the input magnetic field. The magnetic field generation section 530 includes the amplifier circuit 532 and a coil 534.

The amplifier circuit 532 outputs, as a feedback current I_FB, a current in accordance with the detection result of the magnetic sensor 520 for the input magnetic field. When the magnetic resistance element of the magnetic sensor 520 is configured by a bridge circuit including at least one magnetic resistance element, an output of the bridge circuit is connected to each of a pair of input terminals of the amplifier circuit 532. Further, the amplifier circuit 532 outputs, as the feedback current I_FB, a current in accordance with the output of the bridge circuit. The amplifier circuit 532 includes, for example, a transconductance amplifier, and outputs the feedback current I_FB in accordance with the output voltage of the magnetic sensor 520. For example, when a voltage-current conversion coefficient of the amplifier circuit 532 is G, the feedback current I_FB can be calculated as G×S×B.

The coil 534 generates the feedback magnetic field B_FB in accordance with the feedback current I_FB. The coil 534 is wound to surround the magnetic resistance element of the magnetic sensor 520 and the magnetic flux concentrators arranged at both ends of the magnetic resistance element. It is desirable that the coil 534 generates the feedback magnetic field B_FB to be uniform across the entire magnetic sensor 520. For example, when a coil coefficient of the coil 534 is β, the feedback magnetic field B_FB can be calculated as β×I_FB. Here, the feedback magnetic field B_FB is generated with an orientation for cancelling out the input magnetic field B, and thus the magnetic field which is input to the magnetic sensor 520 is reduced to B-B_FB.

Accordingly, the feedback current I_FB is shown by the following Expression.

$$I\_FB = G \times S \times (B - \beta I\_FB) \quad [\text{Math. 1}]$$

When Expression (Math. 1) is solved for the feedback current I_FB, it is possible to calculate the value of the feedback current I_FB in a steady state of the sensor section 300. The following Expression is calculated from Expression (Math. 1), assuming that the magnetic sensitivity S of the magnetic sensor 520 and the voltage-current conversion coefficient G of the amplifier circuit 532 are sufficiently large.

$$I\_FB = \frac{G \times S \times B}{1 + G \times S \times \beta} \cong \frac{B}{\beta} \quad [\text{Math. 2}]$$

The output section 540 outputs an output signal V_xMR in accordance with the feedback current I_FB which is caused to flow for the magnetic field generation section 530 to generate the feedback magnetic field B_FB. For example, the output section 540 has a resistance element with a resistance value R, and outputs a voltage drop, which is caused by the feedback current I_FB flowing through the resistance element, as the output signal V_xMR. In this case, the output signal V_xMR is calculated from Expression (Math. 2) as shown in the following Expression.

$$V\_xMR = R \times I\_FB = \frac{R \times B}{\beta} \quad [\text{Math. 3}]$$

As described above, the sensor section 300 generates the feedback magnetic field that reduces the magnetic field which is input from an outside, and thus the magnetic field which is substantially input to the magnetic sensor 520 is reduced. Thereby, even when the absolute value of the input magnetic field B exceeds 1 μT, it is possible for the sensor section 300 to prevent the detection signal V_xMR from being saturated, for example by using the magnetic resistance element having the characteristic in FIG. 4 as the magnetic sensor 520. The input and output characteristic of such a sensor section 300 is described below.

Figure 6:
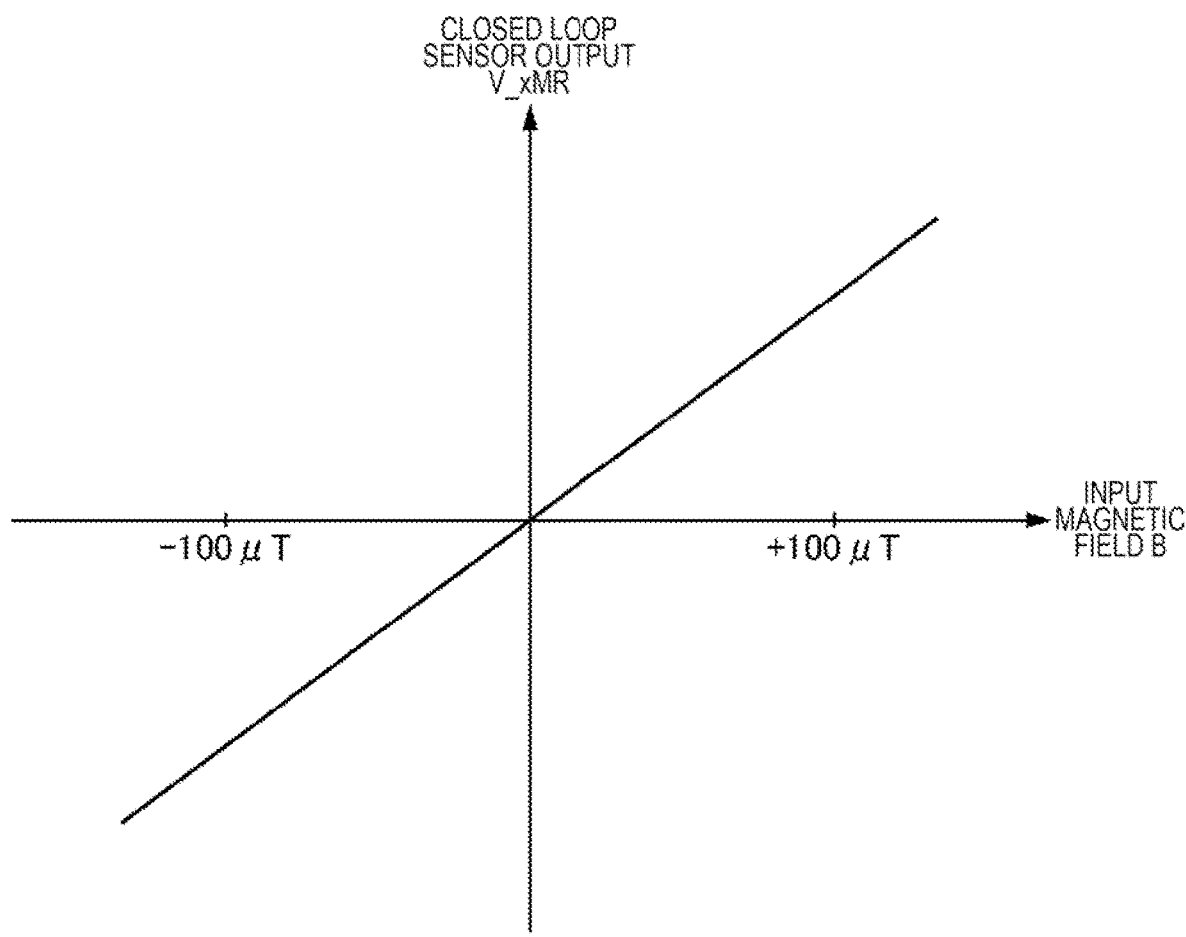
FIG. 6 shows one example of an input and output characteristic of the sensor section 300 according to the present embodiment.

FIG. 6 shows one example of an input and output characteristic of the sensor section 300 according to the present embodiment. In the present drawing, the horizontal axis represents the magnitude B of the input magnetic field which is input to the sensor section 300, and the vertical axis represents the magnitude V_xMR of the detection signal of the sensor section 300. The sensor section 300 has a high magnetic sensitivity and can detect a very small magnetic field of approximately 10 pT. In addition, even when the absolute value of the input magnetic field B exceeds 100 μT, for example, the sensor section 300 can maintain good linearity of the detection signal V_xMR.

That is, the sensor section 300 according to the present embodiment is configured such that the detection result for the input magnetic field B has the linearity, for example, in a predetermined range of the input magnetic field B where the absolute value of the input magnetic field B is smaller than or equal to several hundred μT. Using such a sensor section 300 makes it possible to detect a weak magnetic signal, for example, a magnetocardiographic signal in a simple manner.

Figure 7:
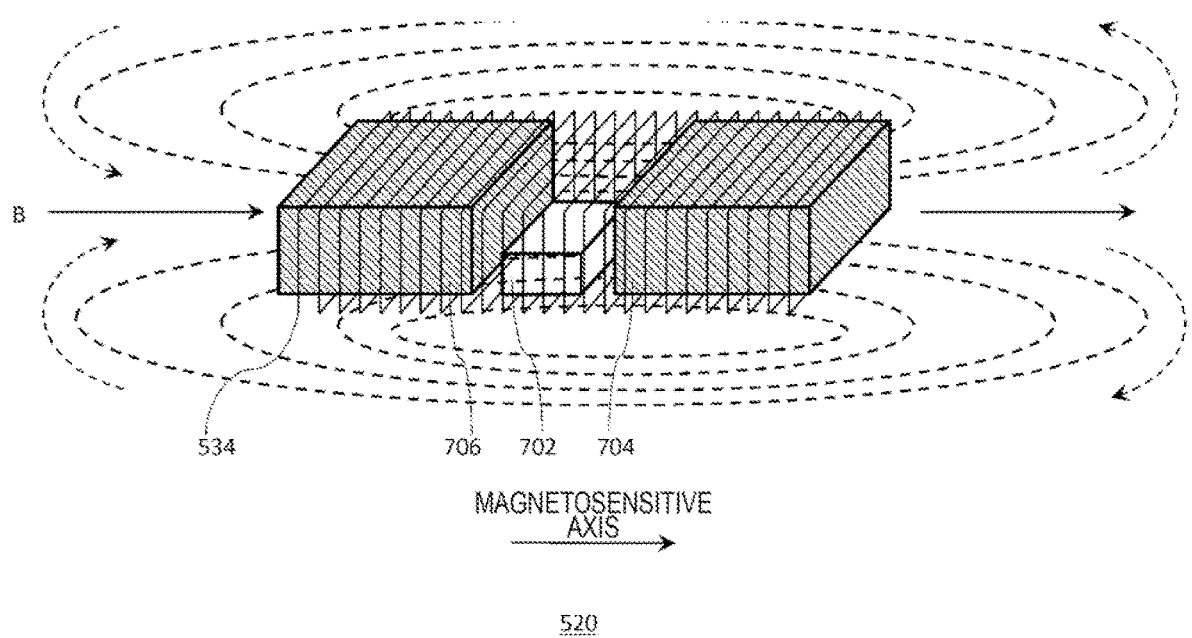
FIG. 7 shows a configuration example of a magnetic sensor 520 according to the present embodiment.

FIG. 7 shows a configuration example of a magnetic sensor 520 according to the present embodiment. As one example, the magnetic sensor 520 according to the present embodiment has a magnetic resistance element 702 and magnetic flux concentrators 704, 706 respectively arranged at one end and the other end of the magnetic resistance element 702. The magnetic flux concentrators 704, 706 are arranged to interpose the magnetic resistance element 702. That is, the magnetic flux concentrators are arranged at both ends of the magnetic resistance element 702. In FIG. 7, the magnetic flux concentrator 704, which is arranged on the right end of the magnetic resistance element 702 along the magnetosensitive axis in front view, is a magnetic flux concentrator provided on a positive side of the magnetosensitive axis, and the magnetic flux concentrator 706, which is arranged on the left end of the magnetic resistance element 702, is a magnetic flux concentrator provided on a negative side of the magnetosensitive axis. When the magnetic field is input, from the negative side toward the positive side of the magnetosensitive axis, to the magnetic flux concentrators 704, 706, a resistance of the magnetic resistance element 702 may increase or decrease. It should be noted that the magnetosensitive axis may be along a magnetization direction fixed by a magnetization fixing layer forming the magnetic resistance element 702. The magnetic flux concentrators 704, 706 are, for example, constituted by a soft magnetic material such as iron. By arranging the magnetic flux concentrators 704, 706, which are constituted by the soft magnetic material, respectively on one end and the other end of the magnetic resistance element 702, it is possible to increase lines of a magnetic force passing through the magnetic resistance element 702, and thus it is possible to enhance the sensitivity of the magnetic sensor 520.

It should be noted that although the present drawing shows the example in which the magnetic flux concentrators are arranged at both of one end and the other end of the magnetic resistance element 702, only either one of one end or the other end of the magnetic resistance element 702 may be provided with the magnetic flux concentrator. However, it is preferable that one end and the other end of the magnetic resistance element 702 are both provided with the magnetic flux concentrators to more enhance the sensitivity of the magnetic sensor 520. In addition, when one end and the other end of the magnetic resistance element 702 are both provided with the magnetic flux concentrators, the position of the magnetic resistance element 702, which is arranged at a narrow position interposed between the two magnetic flux concentrators 704 and 706, is a magnetosensitive section, that is, a spatial sampling point, and thus the magnetosensitive section is clarified, and it is possible to more enhance an affinity with a signal space separation (SSS) method described below. In this way, by using, in each sensor section 300, the magnetic sensor 520 with the magnetic flux concentrators 704 and 706 arranged on both ends of the magnetic resistance element 702, the magnetic field measurement device 10 according to the present embodiment can sample the spatial distribution of the magnetic field, at an extremely narrow (smaller than or equal to 100 μm, for example) position where both ends are interposed between the magnetic flux concentrators in each axial direction, as shown in FIG. 3, and thus a sampling accuracy (a position accuracy) is enhanced in comparison with a case where the spatial distribution of the magnetic field is sampled by using a SQUID coil (up to 2 cm) for measuring the biomagnetic field.

Figure 8:
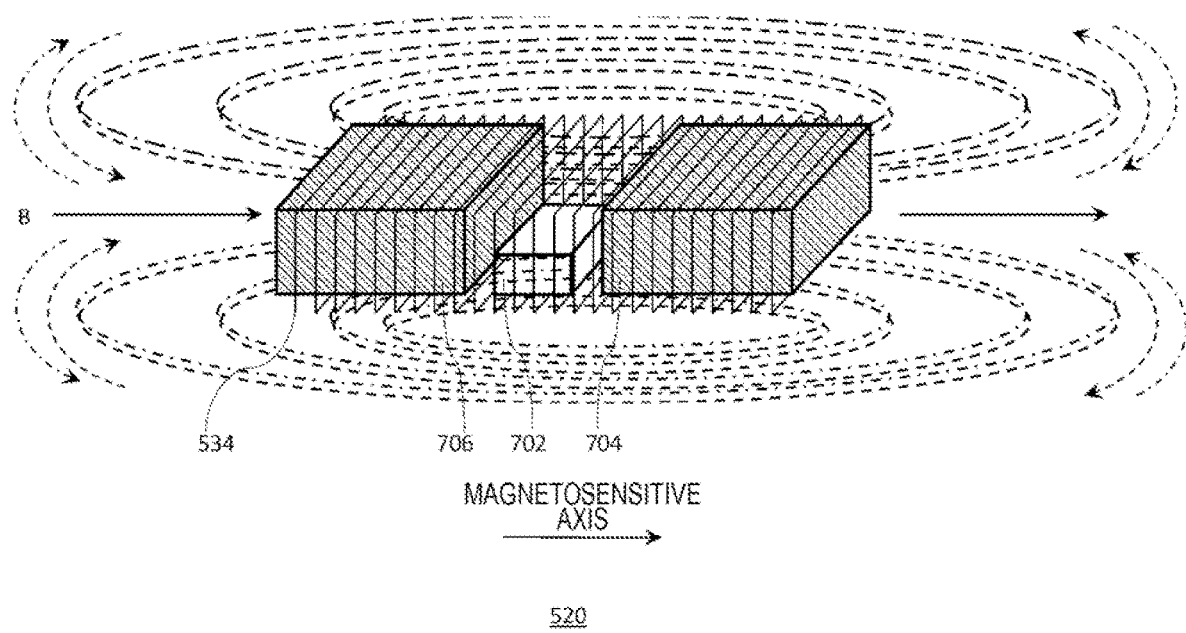
FIG. 8 shows a magnetic flux distribution when a feedback magnetic field is caused to be generated in the magnetic sensor 520 according to the present embodiment.

FIG. 8 shows a magnetic flux distribution when a feedback magnetic field is caused to be generated in the magnetic sensor 520 according to the present embodiment. In FIG. 8, the same signs and numerals are given to members having the same functions and configurations as those in FIG. 7, and the descriptions will be omitted except for the following differences. In the magnetic sensor 520 according to the present embodiment, when the feedback current is supplied to the feedback coil 534, the feedback coil 534 generates the feedback magnetic field, and thus the magnetic flux distribution as shown by the dashed and dotted line the present drawing is generated. The magnetic flux generated by this feedback magnetic field has a spatial distribution to cancel the spatial distribution of the magnetic field which is input to the magnetic resistance element 702 and is magnetically amplified by the magnetic flux concentrators 704 and 706. Therefore, in the magnetic sensor 520, when the magnetic flux concentrators 704 and 706 are arranged at both ends of the magnetic resistance element 702 as shown in the present drawing, the magnetic field distribution at the position of the magnetic resistance element 702 can be accurately cancelled by the feedback magnetic field, and thus it is possible to realize a sensor having high linearity between the input magnetic field and the output voltage.

Figure 9:
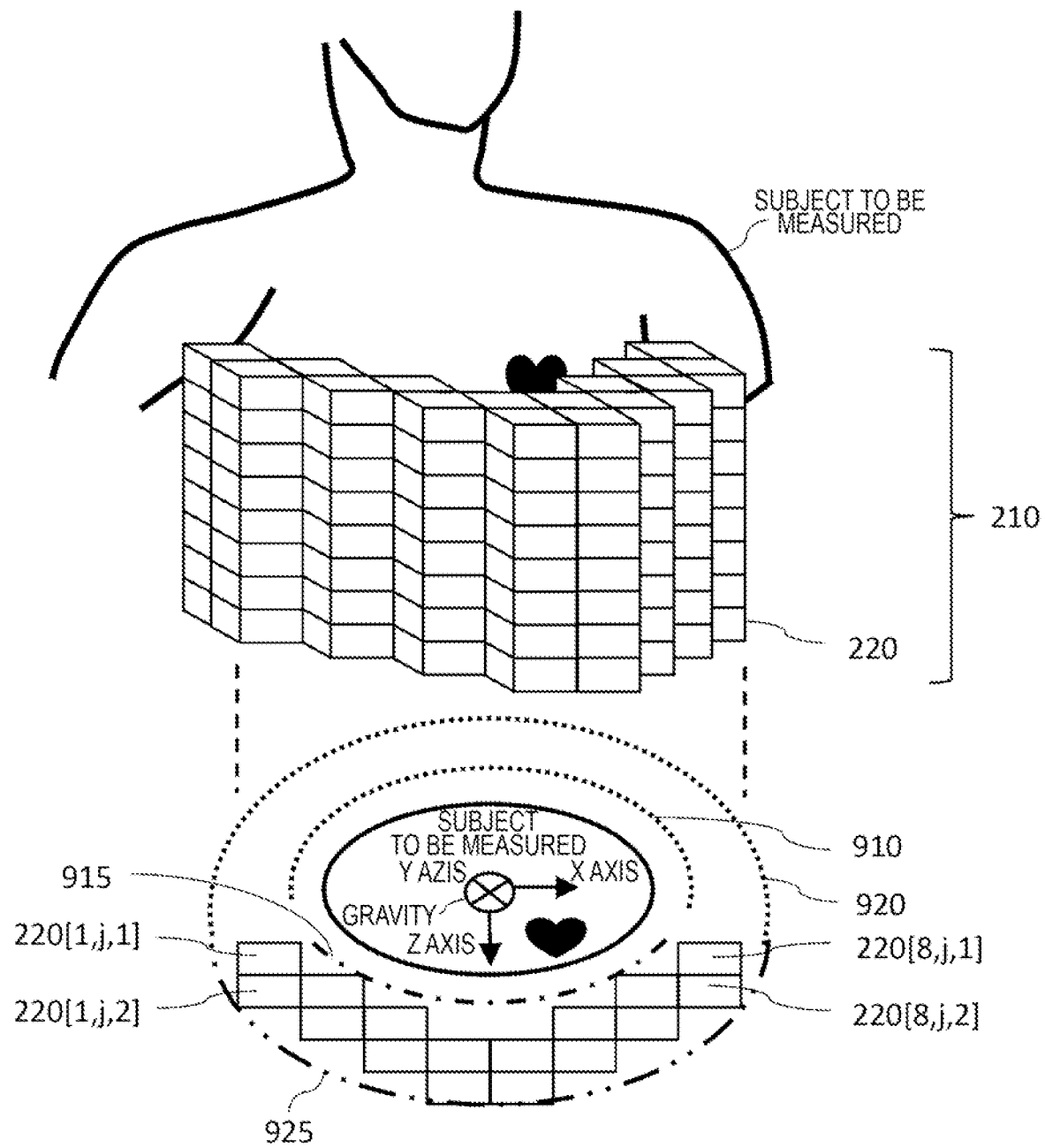
FIG. 9 shows an arrangement example of a plurality of magnetic sensor cells 220 in the magnetic sensor array 210 according to the present embodiment.

FIG. 9 shows an arrangement example of a plurality of magnetic sensor cells 220 in the magnetic sensor array 210 according to the present embodiment. In FIG. 2 and FIG. 3, for convenience of description, the magnetic sensor array 210 is shown to have a planar shape. However, the magnetic sensor array 210 may actually have a curved surface shape which is curved in at least one direction, as shown in the present drawing. Further, the plurality of magnetic sensor cells 220 may be configured by being three-dimensionally arrayed so as to be arranged at grid points included in the curved surface shape. As one example, the magnetic sensor array 210 may be configured by the plurality of magnetic sensor cells 220 being three-dimensionally arrayed to have an arc shape in the cross-sectional view.

That is, the plurality of magnetic sensor cells 220 may be arrayed to have the arc shape, in the cross-sectional view, so as to be along a chest of a subject to be measured, with the gravity of the subject to be measured as the center. In this case, the magnetic sensor cell 220 is arranged at each grid point included in the curved surface shape in a three-dimensional lattice space. It should be noted that here, the grid point is a grid shaped point provided at regular intervals which are predetermined intervals in each of the X direction, the Y direction, and the Z direction. As one example, when viewed from any one direction of the X direction, the Y direction, and the Z direction, each magnetic sensor cell 220 is arranged to be along a curved surface having a protrusion in a direction orthogonal to the one direction. The present drawing shows an example in which each magnetic sensor cell 220 is arranged to be along a curved surface having a protrusion in a positive direction of the Z axis, when viewed from the Y direction. Further, for example, the magnetic sensor array 210 may form the curved surface shape having the protrusion in the positive direction of the Z axis, by respectively arranging the magnetic sensor cells 220 at grid points in the three-dimensional lattice space such that respective vertices of the magnetic sensor cells 220 can possibly be arranged in a negative direction of the Z axis in a range not exceeding a predetermined curved surface having the protrusion in the positive direction of the Z axis.

More specifically, in the cross-sectional view of the present drawing, the plurality of magnetic sensor cells 220 on an internal side (a negative side of the Z axis), that is, the magnetic sensor cells 220 [1, j, 1] to 220 [8, j, 1] are arrayed outside the arc indicated by the dashed and dotted line of reference numeral 915 so as to be arranged outside an inscribed circle of the magnetic sensor array 210 indicated by reference numeral 910. In addition, the plurality of magnetic sensor cells 220 on an external side (a positive side of the Z axis), that is, the magnetic sensor cells 220 [1, j, 2] to 220 [8, j, 2] are arrayed inside the arc indicated by the dashed and two dotted lines of reference numeral 925 so as to be arranged inside a circumscribed circle of the magnetic sensor array 210 indicated by reference numeral 920. The centers of these inscribed circle and the circumscribed circle are common, and match a coordinate origin in a signal separation calculation described below.

In this way, the magnetic sensor array 210 may be configured by the plurality of magnetic sensor cells 220, each of which has the magnetic sensor 520, being arrayed to form a surface covering at least a part of a measurement target. In particular, in the magnetic sensor array 210, the plurality of magnetic sensor cells 220 may be three-dimensionally arrayed so as to be arranged at the grid points between two curved surfaces curved in one direction. Further, such curved surfaces may be formed to be substantially parabolic. This makes it possible for the magnetic sensor array 210 to arrange the sensor section 300 not only in one direction facing the heart but also in multiple directions, and to sense the cardiac magnetic field in multiple directions. In addition, as one example, the magnetic sensor array 210 according to the present embodiment has the magnetic sensor cell 220 formed to have a rectangular parallelepiped shape, and thus it is possible to easily change the shape of the magnetic sensor array 210. That is, the magnetic sensor array 210 according to the present embodiment can have various shapes that can be configured by arranging the magnetic sensor cell 220 at the grid point, and thus has a high degree of freedom in design. Accordingly, as shown in the present drawing, it is possible for the magnetic sensor array 210 to easily form the curved surface shape in the three-dimensional space by arranging the plurality of magnetic sensor cells 220 at the grid points included in the curved surface shape in the three-dimensional space. Further, the magnetic field measurement device 10 measures the magnetic field by arranging the magnetic sensor array 210 such that the chest of the subject to be measured is positioned on the center side of the curved surface, that is, such that the heart which is a magnetic field source to be measured is positioned on the center side of the curved surface. Thereby, by performing the signal space separation by using the measurement data measured at a position close to the heart which is the magnetic field source to be measured (described below), the magnetic field measurement device 10 can perform, with high accuracy, the separation of the magnetic field to be measured and a disturbance magnetic field. It should be noted that in this case, it is preferable that the magnetic sensor array 210 has a curvature of the curved surface substantially the same as a curvature around the chest of the subject to be measured because in doing so, the magnetic field can be measured at a position closer to the heart which is the magnetic field source to be measured.

Figure 10:
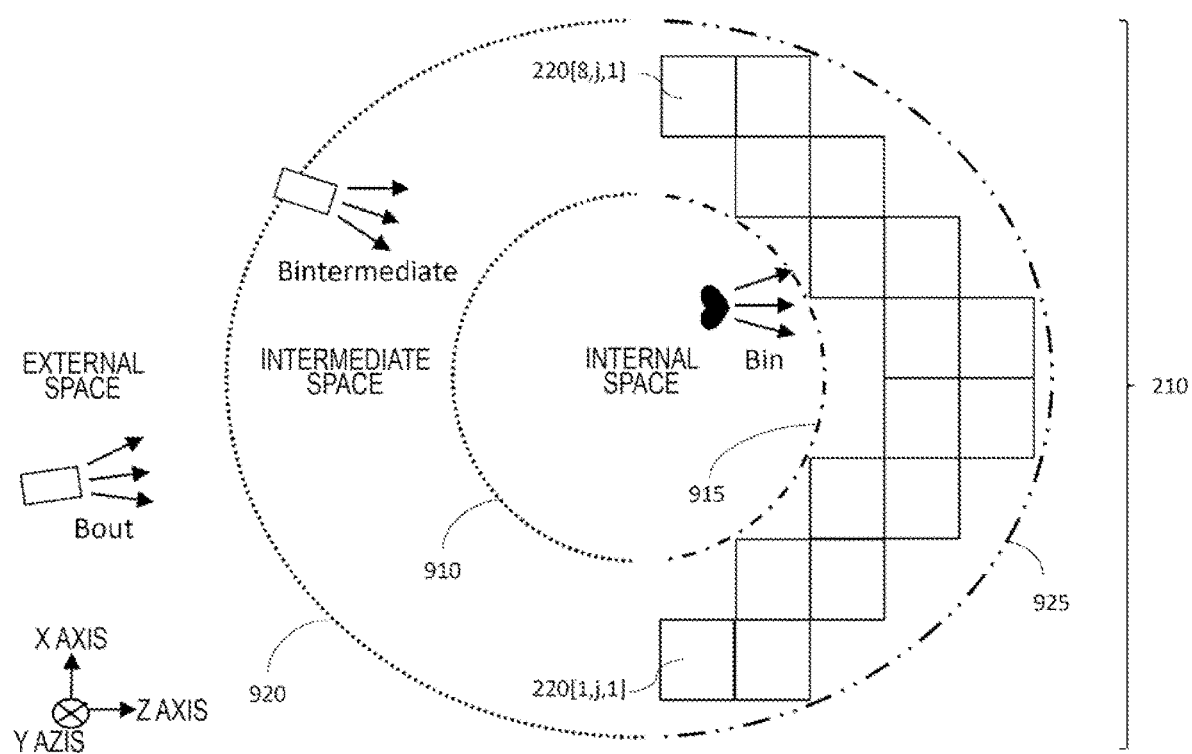
FIG. 10 shows one example of a definition of a space in the magnetic field measurement device 10 according to the present embodiment.

FIG. 10 shows one example of a definition of a space in the magnetic field measurement device 10 according to the present embodiment. An external side of the circle circumscribing the magnetic sensor array 210 indicated by reference numeral 920 is defined as an external space. In addition, an internal side of the circle inscribed in the magnetic sensor array 210 indicated by reference numeral 910 is defined as an internal space. In addition, a space that cannot be clearly distinguished from either the external space or the internal space, such as an internal side of the circle circumscribing the magnetic sensor array 210 indicated by reference numeral 920, which is an external side of the circle inscribed in the magnetic sensor array 210 indicated by reference numeral 910, is defined as an intermediate space. Further, in measuring the cardiac magnetic field, the magnetic sensor array 210 is arranged in the magnetic field measurement device 10 such that the measurement target (that is, the heart of the subject to be measured) is positioned to face the surface formed by the magnetic sensor array 210 in the internal space. In this case, the cardiac magnetic field that is the measurement target is defined as a magnetic field to be measured Bin generated in the internal space.

Here, in a case where the cardiac magnetic field is measured by the magnetic sensor array 210, and the signal separation (the signal separation mentioned here may be referred to as the signal space separation) is performed on the spatial distribution of the magnetic field which is indicated by the measurement data, when the magnetic field to be measured Bin can be accurately separated from the other disturbance magnetic field and taken out, it is possible to more accurately grasp an electrical activity of the heart. However, when the magnetic field measurement device 10 measures the magnetic field to be measured Bin, various environmental magnetic fields may cause interference as the disturbance magnetic field. Such a disturbance magnetic field may include, for example, an external space magnetic field Bout generated in the external space, and an intermediate space magnetic field Bintermediate generated in the intermediate space. Accordingly, in reality, an interference component, which could have not been separated accurately as the disturbance magnetic field and has been remained, may be included, in an estimated value of the magnetic field to be measured Bin on which the signal space separation is performed, that is, internal space data ˆBin (here "ˆ" means an estimated value), in addition to the magnetic field to be measured Bin generated by the electrical activity of the heart. In the first place, such an interference component may include a component caused by the external space magnetic field Bout, which should have been separated as external space data ˆBout, and a component caused by the intermediate space magnetic field Bintermediate which has remained as a component common to both of the internal space data ˆBin and the external space data ˆBout.

Further, the component caused by such an external space magnetic field Bout increases in the magnitude of a sensor error. Here, when the magnetic sensor 520 has the magnetic resistance element 702, an error of the sensor in a main axis sensitivity and cross-axis sensitivity may increase caused by a manufacturing error of the magnetic resistance element 702 or the like. In addition, when the magnetic sensor 520 has magnetic flux concentrators 704 and 706 which are arranged at both of one end and the other end of the magnetic resistance element 702, the error of the sensor in the main axis sensitivity and cross-axis sensitivity may further increase by the relative positional deviation between the magnetic flux concentrators 704 and 706, and the magnetic resistance element 702. For such a reason, the interference component caused by the external space magnetic field Bout cannot be ignored, which is caused by the increase in the sensor error of the magnetic sensor 520. From the internal space data ˆBin on which the signal space separation is performed, the magnetic field measurement device 10 according to the present embodiment removes at least a part of the component caused by the external space magnetic field Bout, particularly, in addition to the remaining interference component, the component caused by the intermediate space magnetic field Bintermediate.

Figure 11:
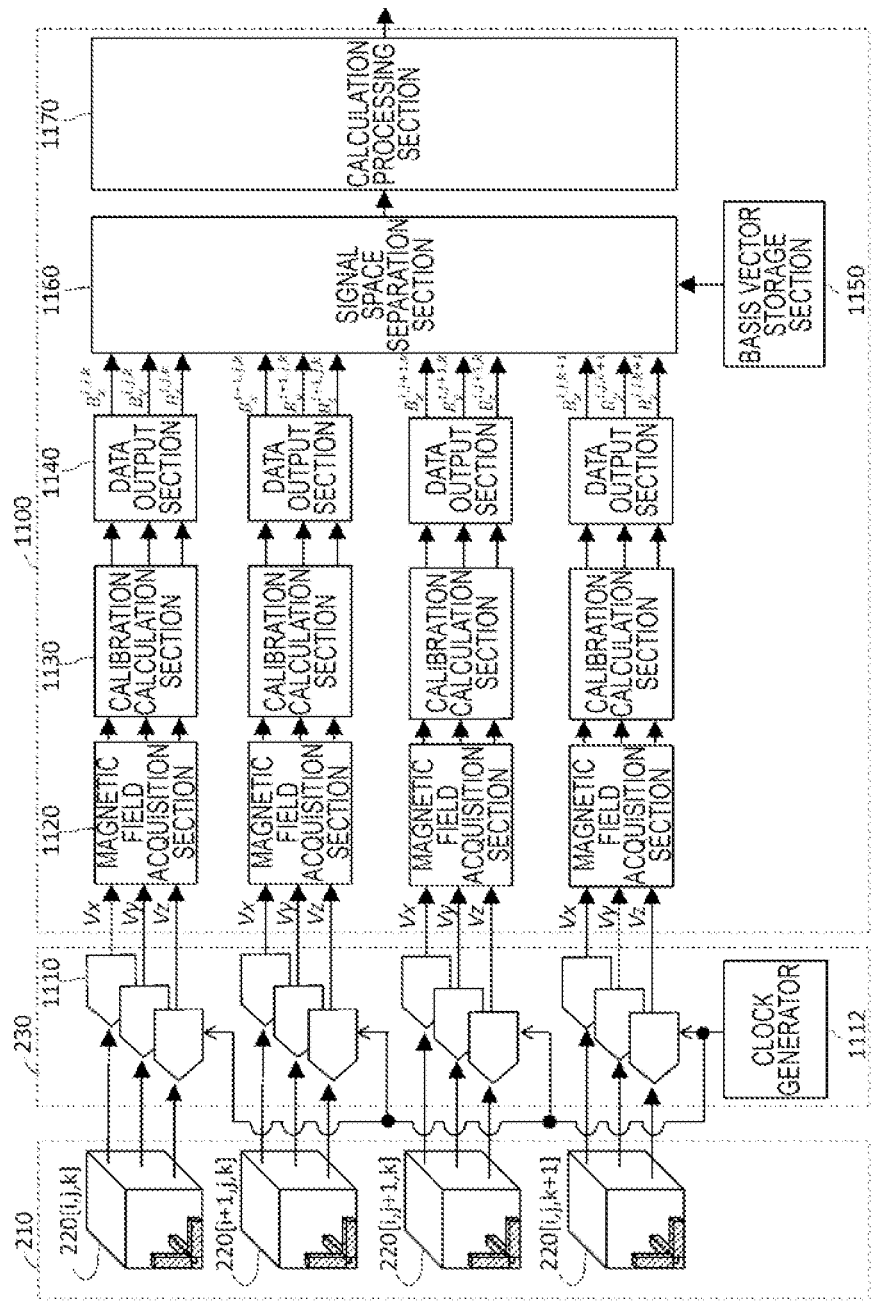
FIG. 11 shows the configuration of the magnetic sensor array 210, a sensor data collection section 230, and a sensor data processing section 1100 according to the present embodiment.

FIG. 11 shows the configuration of the magnetic sensor array 210, a sensor data collection section 230, and a sensor data processing section 1100 according to the present embodiment.

The magnetic sensor array 210 is configured by the plurality of magnetic sensor cells 220, each of which has the magnetic sensor 520, being arrayed to form the surface covering at least a part of the measurement target. As one example, each of the plurality of magnetic sensor cells 220 includes the plurality of sensor sections 300x to z as described above. In the present drawing, among the plurality of magnetic sensor cells 220 of the magnetic sensor array 210 in each dimensional direction, parts relating to positions [i, j, k], [i+1, j, k], [i, j+1, k], and [i, j, k+1] are shown.

The sensor data collection section 230 has a plurality of AD converters 1110 and a clock generator 1112. The plurality of AD converters 1110 are respectively provided to correspond to the plurality of sensor sections 300x to z of the magnetic sensor cell 220, and convert analog detection signals (the sensor output signal V_xMR shown in FIG. 6), which is output by the corresponding sensor section 300, into digital measurement data (Vx, Vy, Vz). Here, Vx, Vy, and Vz are measurement values (representing digital voltage values, for example) obtained by digitally converting the detection signals from the sensor sections 300x, 300y, and 300z.

The clock generator 1112 generates a sampling clock, and supplies a common sampling clock to each of the plurality of AD converters 1110. Further, each of the plurality of AD converters 1110 performs AD conversion according to the common sampling clock supplied from the clock generator 1112. Accordingly, the plurality of AD converters 1110, which perform AD conversion on the respective outputs of the three axis sensor sections 300x to z provided at different positions, all operate in synchronization. This makes it possible for the plurality of AD converters 1110 to perform, at the same time, sampling on the detection results of the three axis sensor sections 300x to z provided in different spaces.

The sensor data processing section 1100 has a plurality of magnetic field acquisition sections 1120, a plurality of calibration calculation sections 1130, and a plurality of data output sections 1140 that are respectively provided to correspond to the plurality of magnetic sensor cells 220, and the sensor data processing section 1100 has a basis vector storage section 1150, a signal space separation section 1160, and a calculation processing section 1170.

Each of the magnetic field acquisition sections 1120 is connected to the three AD converters 1110 that are connected to corresponding magnetic sensor cell 220, and acquire the measurement data measured by each of the sensor sections 300x to z in the plurality of magnetic sensor cells 220 constituting the magnetic sensor array 210. Specifically, the magnetic field acquisition section 1120 may be configured by using a flip-flop or the like that latches and acquires, at a predetermined timing T, the digital measurement data (Vx, Vy, Vz) digitally converted by the AD converter 1110.

The calibration calculation section 1130 is connected to the magnetic field acquisition section 1120, and calibrates the measurement data acquired by the magnetic field acquisition section 1120, by using a calibration parameter. An overview of the calibration for the measurement data performed by the calibration calculation section 1130 is as follows. A magnetic field which is input to the magnetic sensor cell 220 at the position [i, j, k] is defined as B (Bx, By, Bz), and a detection result of the three axis magnetic sensor by the sensor sections 300x, 300y, and 300z is defined as V (Vx, Vy, Vz). In this case, the detection result V of the three axis magnetic sensor can be expressed as in the following Expression, where matrix S represents the magnetic sensor characteristic of the three axis magnetic sensor.

[Math. 4]
$$\begin{pmatrix} Vx \\ Vy \\ Vz \end{pmatrix} = S\begin{pmatrix} Bx \\ By \\ Bz \end{pmatrix} + \begin{pmatrix} Vos,x \\ Vos,y \\ Vos,z \end{pmatrix} = \begin{pmatrix} Sxx & Sxy & Sxz \\ Syx & Syy & Syz \\ Szx & Szy & Szz \end{pmatrix}\begin{pmatrix} Bx \\ By \\ Bz \end{pmatrix} + \begin{pmatrix} Vos,x \\ Vos,y \\ Vos,z \end{pmatrix}$$

Here, Sxx, Syy, and Szz represent sensitivities (main axis sensitivities) of the respective sensor sections 300x, 300y, and 300z in main axis directions, and Sxy, Sxz, Syx, Syz, Szx, and Szy represent sensitivities (cross-axis sensitivities) in other axis directions. In addition, Vos,x, Vos,y, and Vos,z represent offsets of the respective sensor sections 300x, 300y, and 300z. Here, the main axis directions are directions in which the measurements by the sensor sections 300x, 300y, and 300z are mainly performed, and the other axis directions are directions in which the measurement by these sensor sections is not mainly performed. In the magnetic field measurement, the main axis direction is a direction (an input axis direction, a sensitivity axis direction) in which the magnetic sensor shows the highest sensitivity when the magnetic field is input. Further, the other axis directions are defined as axes perpendicular to the main axis direction. For example, when the sensor section 300x performs the measurement in the X axis direction, the main axis direction is the X axis, and the other axis directions are the Y axis direction and the Z axis direction. The magnetic sensor 520 ideally has only the main axis sensitivity, but may have the cross-axis sensitivities caused by process factors or the like. The magnetic sensor 520 also has the cross-axis sensitivities caused by the mutual interference described above. It should be noted that a column vector, which is expressed by three components including the main axis sensitivity and the cross-axis sensitivities of the sensor section 300, is referred to as a sensitivity vector. For example, a sensitivity vector nx of the sensor section 300x is expressed by three components (Sxx, Sxy, Sxz). In this case, the output of the sensor section 300x is an inner product between the input magnetic field to the sensor and the sensitivity vector nx. In addition, similarly, a sensitivity vector ny of the sensor section 300y is expressed by three components (Syx, Syy, Syz), and a sensitivity vector nz of the sensor section 300z is expressed by three components (Szx, Szy, Szz).

A detection result of each of the sensor sections 300 has, in a range of the input magnetic field to be detected, the linearity for the input magnetic field, and thus each element of the matrix S is a substantially constant coefficient independent of the magnitude of the input magnetic field B. In addition, even when the sensor section 300 has the cross-axis sensitivities, as long as the detection result of the sensor section 300 has the linearity, each element of the matrix S is the substantially constant coefficient independent of the magnitude of the input magnetic field B.

Accordingly, by using an inverse matrix S-1 of the matrix S and the offsets (Vos,x, Vos,y, Vos,z), as in the following Expression, the calibration calculation section 1130 can convert the measurement data V (Vx, Vy, Vz) into the magnetic field measurement data B (Bx, By, Bz) indicating the original input magnetic field. That is, the calibration calculation section 1130 calibrates the digital measurement data V from the magnetic field acquisition section 1120 by using the main axis sensitivity, cross-axis sensitivities, and the offsets. Thereby, the calibration calculation section 1130 corrects the offsets, the sensitivity in the main axis direction, and the sensitivities in the other axis directions. It should be noted that this conversion is also made even when the sensor sections 300x to z have the magnetic flux concentrators described above. This is because the magnetic sensor cell 220 is configured as the three axis magnetic sensor using the sensor sections 300x to z, and because the conversion using linear algebra is possible. It should be noted that by providing a high-pass filter or the like in a section from the output of the sensor section 300 up to the calibration calculation section 1130, the calibration for the offsets may be omitted when the measurement data V is an AC component. That is, the calibration calculation section 1130 may calibrate the digital measurement data V from the magnetic field acquisition section 1120 by using at least any of the main axis sensitivity, cross-axis sensitivities, and the offsets. It should be noted that these calibration parameters may be calculated by measuring known DC or AC magnetic fields in advance. In addition, the calibration calculation section 1130 in the present embodiment only needs to be capable of calibrating the output from each magnetic sensor cell 220 to components expressed by a coordinate system which is formed by three independent vectors, and does not necessarily need to correct the output to three axis components expressed by a coordinate system (what is known as the Cartesian coordinate system) with three vectors orthogonal to each other. That is, when all the magnetic sensor cells 220 measure the same magnetic field, the calibration calculation section 1130 corresponding to each magnetic sensor cell 220 may calibrate the digital measurement data V from the corresponding magnetic field acquisition section 1120, to the same magnetic field measurement data B expressed by independent three axis components.

[Math. 5]
$$\begin{pmatrix} Bx \\ By \\ Bz \end{pmatrix} = S^{-1}\left\{\begin{pmatrix} Vx \\ Vy \\ Vz \end{pmatrix} - \begin{pmatrix} Vos,x \\ Vos,y \\ Vos,z \end{pmatrix}\right\}$$

The calibration calculation section 1130 uses environmental magnetic field measurement data to calculate the inverse matrix S-1 of the matrix S and the offsets (Vos,x, Vos,y, Vos,z), converts the magnetic field measurement data acquired by the magnetic field acquisition section 1120 into the magnetic field measurement data B by using these calibration parameters, and supplies the magnetic field measurement data B to the data output section 1140.

As described above, each sensor section 300 has the linearity, and thus the calibration calculation sections 1130 can convert the measurement data into the magnetic field measurement data B by using the substantially constant coefficient. That is, substantially constant coefficients used by the calibration calculation section 1130 can be determined as a set of calibration parameters by using the environmental magnetic field data.

The data output section 1140 supplies, to the signal space separation section 1160, the magnetic field measurement data B calibrated by the calibration calculation section 1130.

The basis vector storage section 1150 stores in advance basis vectors required for the signal space separation section 1160 to perform the signal separation on the magnetic field measurement data B, and supplies the required basis vectors to the signal space separation section 1160. Such basis vectors may be calculated from the position and the magnetic sensitivity of each magnetic sensor 520.

Based on the position and the magnetic sensitivity of each magnetic sensor 520, the signal space separation section 1160 performs the signal separation to separate, into the internal space data ^Bin and the external space data ^Bout, the spatial distribution of the magnetic field which is indicated by the measurement data, that is, the spatial distribution of the magnetic field which is indicated by the magnetic field measurement data B obtained by calibrating the digital measurement data V. For example, the signal space separation section 1160 performs the signal separation on the spatial distribution of the magnetic field based on the basis vectors calculated from orthonormal functions, and the position and the magnetic sensitivity of each magnetic sensor 520. In this case, the signal space separation section 1160 may perform the signal separation on the spatial distribution of the magnetic field, through series expansion of the basis vectors. More specifically, the signal space separation section 1160 may calculate expansion coefficients of the basis vectors by a method of least squares. It should be noted that such orthonormal functions may be expressed with spherical harmonics. The details of signal separation are described below. In this way, the signal space separation section 1160 performs the signal separation to separate, into the internal space data ^Bin and the external space data ^Bout, the spatial distribution of the magnetic field which is indicated by the magnetic field measurement data B. The signal space separation section 1160 supplies, to the calculation processing section 1170, the magnetic field measurement data B which is the data before the signal separation, and the internal space data ^Bin and the external space data ^Bout which are the data after the signal separation.

The calculation processing section 1170 removes, from the internal space data ^Bin, at least a part of the variation component common to the magnetic field measurement data B that indicates the spatial distribution of the magnetic field which is indicated by the measurement data B, and the external space data ^Bout. For example, the calculation processing section 1170 respectively calculates a time domain basis C based on the magnetic field measurement data B and a time domain basis Cout based on the external space data ^Bout, by respectively performing singular value decomposition on the magnetic field measurement data B and the external space data ^Bout. Further, the calculation processing section 1170 extracts the common variation component based on a correlation between the time domain basis C based on the magnetic field measurement data B and the time domain basis Cout based on the external space data ^Bout. In this case, for example, the calculation processing section 1170 may calculate a coefficient of the correlation by performing the singular value decomposition on a covariance of the time domain basis C based on the magnetic field measurement data B and the time domain basis Cout based on the external space data ^Bout, and extract, as the common variation component, a component of which the coefficient of the correlation exceeds a predetermined threshold value. For example, in this way, the calculation processing section 1170 may extract the common variation component by performing principal component analysis on the time domain basis C based on the magnetic field measurement data B and the time domain basis Cout based on the external space data ^Bout. Further, the calculation processing section 1170 removes, from the internal space data ^Bin, at least a part of the variation component that is common to the magnetic field measurement data B and the external space data ^Bout and that is extracted in this way, and outputs the at least removed part of the variation component. The details of such calculation processing are also described below.

Figure 12:
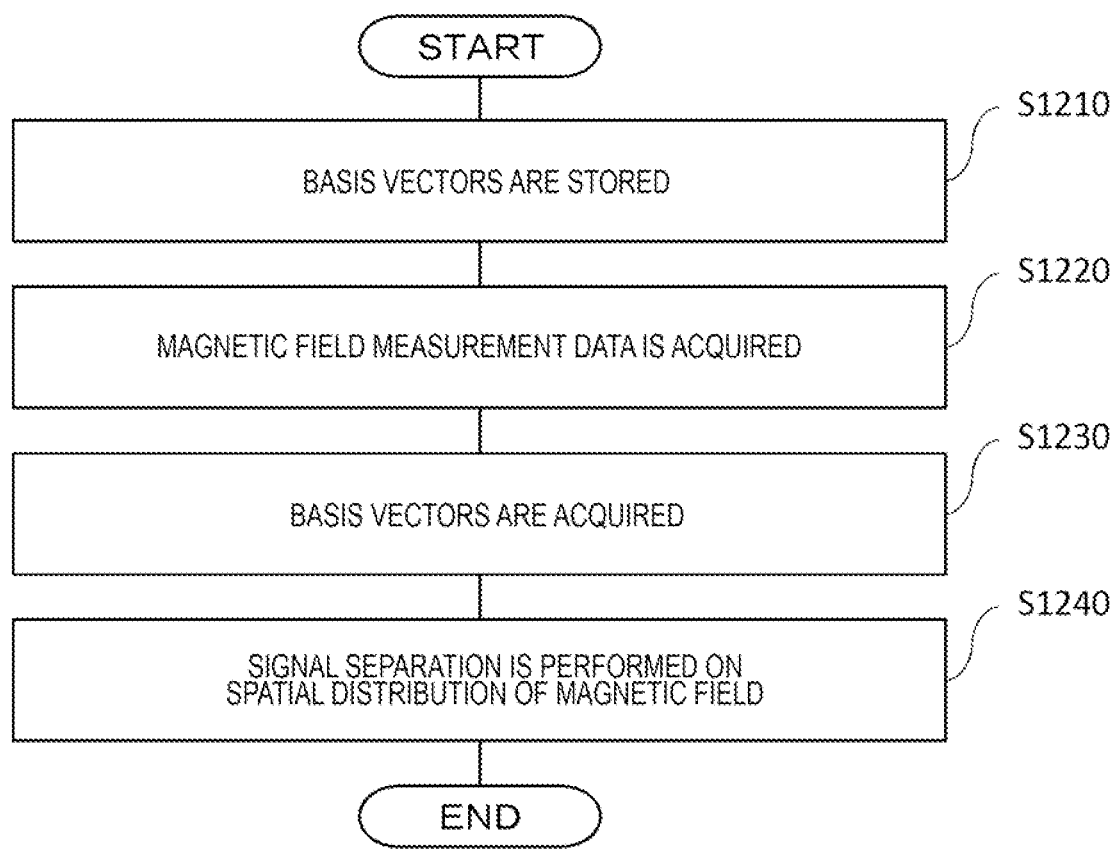
FIG. 12 shows a flow in which the magnetic field measurement device 10 according to the present embodiment performs a signal separation on a spatial distribution of a magnetic field.

FIG. 12 shows a flow in which the magnetic field measurement device 10 according to the present embodiment performs a signal separation on a spatial distribution of a magnetic field. In step 1210, the basis vector storage section 1150 stores the basis vectors. As one example, before the measurement of the magnetic field to be measured, the basis vector storage section 1150 stores, as the basis vectors, signal vectors output respectively by the plurality of magnetic sensors 520 when the magnetic sensor array 210 detects the magnetic field having the spatial distribution of the spherical harmonics. That is, the basis vectors may be calculated in advance, by the calculation from the position and the sensitivity vector of each magnetic sensor 520 in the magnetic sensor array 210, and may be stored in the basis vector storage section 1150. That is, the basis vector storage section 1150 stores, as the basis vectors, magnetic field signal vectors obtained by performing the spatial sampling on the spherical harmonics when a predetermined point in a space is designated as the coordinate origin. In other words, by the calculation from the position and the sensitivity vector of each magnetic sensor 520, the basis vector storage section 1150 calculates in advance the magnetic field signal vectors expressing a magnetic field of a space with two subspaces (a signal source space which is the measurement target, and a disturbance space) based on the series expansion of the spherical harmonics, and stores the calculated magnetic field signal vectors as the basis vectors. Here, the spherical harmonics are functions obtained by restricting, to a unit sphere, a homogeneous polynomial that is a solution to an n-dimensional Laplace equation, and has orthonormality on the sphere. It should be noted that the present drawing shows, as one example, a case where step 1210, in which the basis vector storage section 1150 stores the basis vectors, is defined as the first step in the flow of the signal separation on the spatial distribution of the magnetic field performed by the magnetic field measurement device 10. However, the basis vector storage section 1150 may store in advance the basis vectors, before the flow of the signal separation on the spatial distribution of the magnetic field performed by the magnetic field measurement device 10. In addition, the basis vector storage section 1150 may store, as the basis vectors, the signal vectors predetermined by a simulation result or the like.

Next, in step 1220, the signal space separation section 1160 acquires, from the data output section 1140, the magnetic field measurement data B measured by the magnetic sensor array 210 and calibrated by the calibration calculation section 1130.

In addition, in step 1230, the signal space separation section 1160 acquires, from the basis vector storage section 1150, the signal vectors stored as the basis vectors by the basis vector storage section 1150 in step 1210. It should be noted that in this flow, either one of step 1220 or step 1230 may be performed before the other.

In step 1240, the signal space separation section 1160 performs the series expansion of the spatial distribution of the magnetic field which is indicated by the magnetic field measurement data B acquired in step 1220, by using the signal vectors acquired in step 1230 as the basis vectors. Further, the signal space separation section 1160 performs the signal separation to separate the spatial distribution of the magnetic field into the internal space data ^Bin (an estimated value of the magnetic field to be measured) and the external space data ^Bout (an estimated value of the disturbance magnetic field), based on the vectors obtained by the series expansion. it should be noted that the orthonormal functions may be spherical harmonics. In addition, in performing the signal separation, the signal space separation section 1160 calculates series expansion coefficients of the basis vectors by the method of least squares. The details of this are described below.

By using a potential V(r) satisfying a Laplace equation $\Delta V(r)=0$, a static magnetic field B(r) is obtained as a spatial gradient (gradient) of the potential V(r) as in the following Expression. Here, r represents a position vector representing a position with respect to the coordinate origin, $\Delta$ represents a Laplacian, $\mu$ represents permeability, and $\nabla$ represents a vector differential operator.

$$B(r) = -\mu \nabla V(r) \quad [\text{Math. 6}]$$

Further, generally, a solution to the Laplace equation is in a form of the series expansion using spherical harmonics Yl, m($\theta$, $\varphi$) which are functions of an orthonormal function system, and thus the potential V(r) can be expressed as in the following Expression. Here, |r| represents an absolute value (the distance from the coordinate origin) of the position vector r, $\theta$ and $\varphi$ represent two declinations of spherical coordinate, l represents an azimuthal quantum number, m represents a magnetic quantum number, $\alpha$ and $\beta$ represent multipole moments, and Lin and Lout are the numbers of series respectively in closer and farther spaces in the magnetic sensor array 210 when viewed from the subject. The azimuthal quantum number l is a positive integer, and the magnetic quantum number m is an integer in a range from $-1$ to $+1$. That is, when l is 1, for example, m is $-1$, 0, and 1, and when l is 2, for example, m is $-2$, $-1$, 0, 1, and 2. It should be noted that no single magnetic pole exists in the magnetic field, and thus the azimuthal quantum number l starts from 1 rather than 0 in Expression (Math. 7). The first term in Expression (Math. 7) is a term inversely proportional to the distance from the coordinate origin, and represents a potential existing in the closer space in the magnetic sensor array 210 when viewed from the subject. In addition, the second term in Expression (Math. 7) is a term proportional to the distance from the coordinate origin, and represents a potential existing in the farther space in the magnetic sensor array 210 when viewed from the subject to be measured.

$$V(r) = \sum_{l=1}^{Lin} \sum_{m=-l}^{l} \alpha_{l,m} \left( \frac{1}{|r|^{l+1}} Y_{l,m}(\theta, \phi) \right) + \sum_{l=1}^{Lout} \sum_{m=-l}^{l} \beta_{l,m} (|r|^l Y_{l,m}(\theta, \phi)) \quad [\text{Math. 7}]$$

Accordingly, according to Expression (Math. 6) and Expression (Math. 7), the static magnetic field B(r) can be expressed by the following Expression. Here, the first term in Expression (Math. 8) represents the magnetic field source existing in the closer space in the magnetic sensor array 210 when viewed from the subject to be measured, that is, the cardiac magnetic field (the magnetic field to be measured) made by the electrical activity of the heart. In addition, the second term in Expression (Math. 8) represents the disturbance magnetic field made by the magnetic field source existing in the farther space in the magnetic sensor array 210 when viewed from the subject to be measured.

$$B(r) = -\mu \sum_{l=1}^{Lin} \sum_{m=-l}^{l} \alpha_{l,m} \nabla \left( \frac{1}{|r|^{l+1}} Y_{l,m}(\theta, \phi) \right) - \quad [\text{Math. 8}]$$

-continued
$$\mu \sum_{l=1}^{Lin} \sum_{m=-l}^{l} \beta_{l,m} \nabla (|r|^l Y_{l,m}(\theta, \phi))$$

When the solution to the Laplace equation is expressed in a form of the series expansion using the spherical harmonics, the general solution of such will be infinite series; however, what needs to be obtained is a sufficient signal-to-noise ratio (SNR, that is, a ratio of a signal of the magnetic field to be measured, to the disturbance magnetic field and sensor noise) for measuring the biomagnetic field, which is regarded as being actually and sufficiently expressible with a series of about 10 terms. In addition, as the series for signal space separation in magnetoencephalogram, approximately Lin=8 and Lout=3 are generally used. Accordingly, also in the present embodiment, values approximate to these described above may be used for Lin and Lout. However, the Lin and Lout values are not limited to these, and may be any numerical values that are sufficient for sufficiently suppressing the disturbance magnetic field and calculating only the magnetic field to be measured.

Here, for all N sensors used in the magnetic sensor array 210, al,m and bl,m are defined as in the following Expression. Here, n1, n2, ... nN represent sensitivity vectors of the respective sensor sections. It should be noted that these al,m and bl,m are vectors with the number of dimensions obtained by multiplying the number of magnetic sensor cells 220 by three (because there are sensor sections 300x, y, and z). That is, the number of dimensions of the vector corresponds to the number of all sensors. As one example, the vectors (al,m, bl,m) are calculated by using data obtained by the calibration calculation section 1130 correcting the output of each of the magnetic sensor cells 220. The values of al,m and bl,m, which are obtained by calculation including correction on the sensitivities of the sensor section 300x, y, and z in the main axis direction and in the other axis directions (the corrected sensitivity vector) in this way, are stored in the basis vector storage section 1150. The magnetic field measurement device 10 according to the present embodiment, in which the basis vector storage section 1150 stores the values of al,m and bl,m which are obtained by calculation including correction on the magnetic sensitivities (the main axis sensitivity, and the cross-axis sensitivities), can correct, during the operation, the magnetic sensitivity of each magnetic sensor cell 220 (the main axis sensitivity, and the cross-axis sensitivities) by the calibration calculation section 1130 correcting the data acquired by the magnetic field acquisition section 1120. In addition, as another example, when the basis vector storage section 1150 stores default values of al,m and bl,m (from uncorrected sensitivity vector) without correction on the magnetic sensitivity (the main axis sensitivity, and the cross-axis sensitivities), the calibration calculation section 1130 converts the output from each magnetic sensor cell 220 into data with the magnetic sensitivity corrected to match the default sensitivity vector of each sensor section as in Expression (Math. 5), and output the converted data to the data output section 1140, and then the calculation by the signal space separation section 1160 is implemented.

$$\alpha_{l,m} = -\mu \begin{bmatrix} \nabla\left(\frac{1}{r_1^{l+1}} Y_{l,m}(\theta_1, \phi_1)\right) \cdot n_1 \\ \nabla\left(\frac{1}{r_2^{l+1}} Y_{l,m}(\theta_2, \phi_2)\right) \cdot n_2 \\ \vdots \\ \nabla\left(\frac{1}{r_N^{l+1}} Y_{l,m}(\theta_N, \phi_N)\right) \cdot n_N \end{bmatrix}$$ [Math. 9]

$$b_{l,m} = -\mu \begin{bmatrix} \nabla(r_1^l Y_{l,m}(\theta_1, \phi_1)) \cdot n_1 \\ \nabla(r_2^l Y_{l,m}(\theta_2, \phi_2)) \cdot n_2 \\ \vdots \\ \nabla(r_N^l Y_{l,m}(\theta_N, \phi_N)) \cdot n_N \end{bmatrix}$$

In this way, $a_{l,m}$ and $b_{l,m}$ are defined, and thus a sensor output vector $\Phi$ which is output from each magnetic sensor cell 220 at a certain time point can be expressed in the following Expression.

$$\Phi = \sum_{l=1}^{Lin} \sum_{m=-l}^{l} \alpha_{l,m} a_{l,m} + \sum_{l=1}^{Lout} \sum_{m=-l}^{l} \beta_{l,m} b_{l,m}$$

Further, Sin, Sout, Xin, and Xout are each defined in the following manner. That is, Sin is defined as a vector with a total of Lin×(Lin+2) columns in which vectors [a] that are respectively obtained with integers m=−1 to 1 with each of l=1 to l=Lin, are arranged in columns in order. In addition, Sout is defined as a vector with a total of Lout×(Lout+2) columns in which vectors [b] that are respectively obtained with integers m=−1 to 1 with each of l=1 to l=Lout, are arranged in columns in order. In addition, Xin is defined as a vector with a total of Lin×(Lin+2) rows as a result of transposing a vector in which multipole moments $\alpha_{l,m}$ that are respectively obtained with integers m=−1 to 1 with each of l=1 to l=Lin, are arranged in columns in order. In addition, Xout is defined as a vector with a total of Lout×(Lout+2) rows as a result of transposing a vector in which multipole moments $\beta_{l,m}$ that are respectively obtained with integers m=−1 to 1 with each of l=1 to l=Lin, are arranged in columns in order.

$Sin = [a_{1,-1} a_{1,0} a_{1,+1} \ldots a_{Lin,Lin}]$ $Sout = [b_{1,-1} b_{1,0} b_{1,+1} \ldots b_{Lout,Lout}]$ $xin = [\alpha_{1,-1} \alpha_{1,0} \alpha_{1,+1} \ldots \alpha_{Lin,Lin}]^t$ $xout = [\beta_{1,-1} \beta_{1,0} \beta_{1,+1} \ldots \beta_{Lout,Lout}]^t$ [Math. 11]

Then, the sensor output vector $\Phi$ can be expressed in a form of an inner product of the matrix S and a column vector X as in the following Expression. Here, the matrix S represents the basis vectors, which are acquired by the signal space separation section 1160 from the basis vector storage section 1150, in step 1230, for example. In addition, the column vector X represents coefficients related to the basis vectors.

$$\Phi = SX = [Sin \ Sout] \begin{bmatrix} Xin \\ Xout \end{bmatrix}$$ [Math. 12]

The signal space separation section 1160 according to the present embodiment determines the column vector X satisfying $\Phi = SX$ with least squares approximation by using the following Expression, based on a model formula of the sensor output vector $\Phi$ obtained by this Expression (Math. 12), in step 1240. This makes it possible for the signal space separation section 1160 to solve the spatial distribution of the magnetic field, in step 1240. That is, the signal space separation section 1160 can estimate the spatial distribution of the magnetic field. That is, by setting the sensor output vector $\Phi$ as the magnetic field measurement data B in Expression (Math. 12), the signal space separation section 1160 can estimate the magnetic field to be measured Bin with the internal space data ^Bin=SinXin, and the disturbance magnetic field with the external space data ^Bout=SoutXout. In this case, the signal space separation section 1160 may issue an alert indicating that the magnetic field to be measured Bin cannot be estimated with high accuracy, when the magnitude of the external space data ^Bout exceeds a predetermined range. This makes it possible to prevent, in advance, the magnetic field measurement device 10 from measuring the magnetic field to be measured Bin in situations such as a case where the apparatus is under failure, and a case where a large disturbance magnetic field exists to the degree that the magnetic field to be measured Bin cannot be estimated with high accuracy. In this case, for example, the signal space separation section 1160 may determine that the magnitude of the disturbance magnetic field exceeds a predetermined range when the magnitude of any of each component of SoutXout exceeds a predetermined threshold value, or may determine that the magnitude of the disturbance magnetic field exceeds a predetermined range when a sum or an average of the magnitude of each component of SoutXout exceeds a predetermined threshold value.

$$X = \begin{bmatrix} Xin \\ Xout \end{bmatrix} = (S^t S)^{-1} S^t \Phi$$ [Math. 13]

Further, the signal space separation section 1160 supplies, to the calculation processing section 1170, the magnetic field measurement data B, which is the data before the signal separation and is acquired in step 1220, and the internal space data ^Bin and the external space data ^Bout, which are the data after the signal separation in step 1240.

Thereby, with the magnetic field measurement device 10 according to the present embodiment, the signal separation can be performed to separate, into the internal space data ^Bin and the external space data ^Bout, the spatial distribution of the magnetic field which is indicated by the magnetic field measurement data B measured by using the magnetic sensor array 210 that is configured by the plurality of magnetic sensor cells 220, each of which has the magnetic sensor 520, being arrayed to form the surface covering at least a part of the measurement target. Here, each of the plurality of sensor sections 300 includes magnetic flux concentrators, and thus it is possible to enhance the magnetic sensitivity of the sensor section 300, and to clarify spatial sampling points, and it is possible to enhance the affinity with the signal space separation method.

Figure 13:
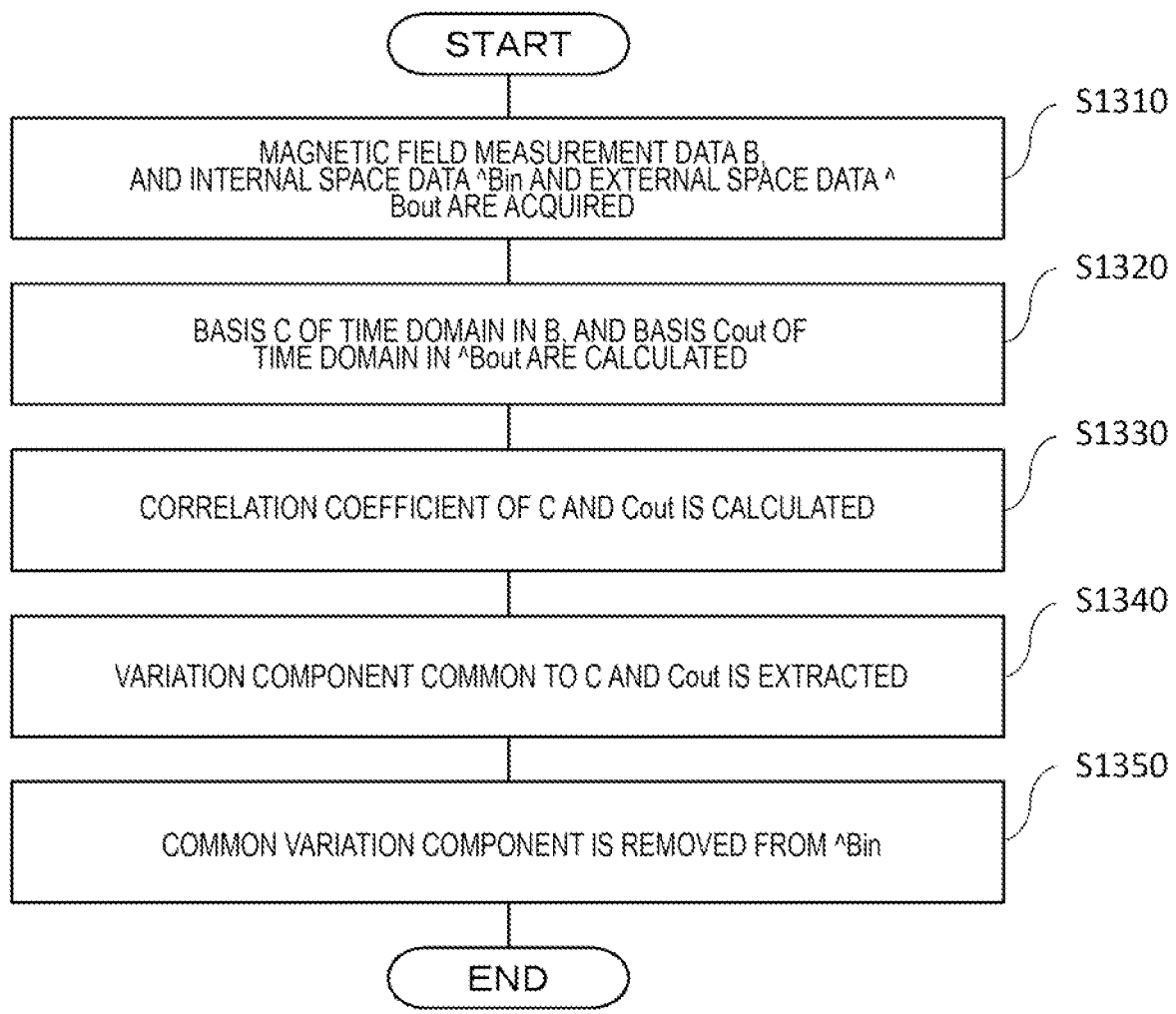
FIG. 13 shows one example of a flow in which the magnetic field measurement device 10 according to the present embodiment removes a remaining interference component from internal space data ^Bin obtained by a signal space separation.

FIG. 13 shows one example of a flow in which the magnetic field measurement device 10 according to the present embodiment removes a remaining interference component from internal space data ^Bin obtained by a signal space separation.

In step 1310, the magnetic field measurement device 10 acquires, as time-series data, the magnetic field measurement data B, and the internal space data ^Bin and the external space data ^Bout. For example, the calculation processing section 1170 acquires, from the signal space separation section 1160 in chronological order, the magnetic field measurement data B acquired by the signal space separation section 1160 in step 1220, and the internal space data ^Bin and the external space data ^Bout obtained by the signal separation in step 1240. That is, from the magnetic field measurement data B, the internal space data ^Bin and the external space data ^Bout are respectively calculated at each time point t1, t2, . . . tn, and are acquired as B=[B (t1) B (t2) . . . B (tn)]. Here, the magnetic field measurement data B, the internal space data ^Bin and the external space data ^Bout are respectively matrices in which the vertical direction corresponds to each magnetic sensor cell, and the horizontal direction corresponds to each time point.

Here, the acquired pieces of data can be defined respectively as in the following Expression. That is, the magnetic field measurement data B may include the magnetic field to be measured Bin generated in the internal space, the intermediate space magnetic field Bintermediate generated in the intermediate space, and the external space magnetic field Bout generated in the external space. In addition, the internal space data ^Bin may include components caused by the magnetic field to be measured Bin and the intermediate space magnetic field Bintermediate, and a component caused by the external space magnetic field Bout. Here, α represents a coefficient, and E represents the magnitude of the sensor error of the magnetic sensor 520. In addition, the external space data ^Bout may include components included in the intermediate space magnetic field Bintermediate and the external space magnetic field Bout.

$$B = B_{in} + B_{intermediate} + B_{out}$$

$$\widehat{B_{in}} = B_{in} + \alpha \cdot B_{intermediate} + \vartheta \cdot B_{out}$$

$$\widehat{B_{out}} = \beta \cdot B_{intermediate} + B_{out} \quad \text{[Math. 14]}$$

In step 1320, the magnetic field measurement device 10 calculates the time domain basis C based on the magnetic field measurement data B and the time domain basis Cout based on the external space data ^Bout. For example, the calculation processing section 1170 respectively calculates the basis time domain C based on the magnetic field measurement data B and the time domain basis Cout based on the external space data ^Bout, by respectively performing the singular value decomposition on the magnetic field measurement data B and the external space data ^Bout. More specifically, the calculation processing section 1170 calculates the basis C and the basis Cout by the following Expression, respectively. That is, the calculation processing section 1170 divides and normalizes, by the Frobenius norm, a transposed matrix of the magnetic field measurement data B in a certain time domain, to apply the singular value decomposition. Further, the calculation processing section 1170 calculates a left singular vector U after the singular value decomposition, as the time domain basis C based on the magnetic field measurement data B. Similarly, the calculation processing section 1170 divides and normalizes, by the Frobenius norm, a transposed matrix of the external space data ^Bout in a certain time domain, to apply the singular value decomposition. Further, the calculation processing section 1170 calculates a left singular vector Uout after the singular value decomposition, as the time domain basis Cout based on the external space data ^Bout.

$$\frac{B^T}{\|B\|_F} = U \sum V_i^T, \quad U = C \quad \text{[Math. 15]}$$

$$\frac{\hat{B}_{out}^T}{\|\hat{B}_{out}\|_F} = U_{out} \sum\nolimits_{out} V_{out}^T, \quad U_{out} = C_{out}$$

In step 1330, the magnetic field measurement device 10 calculates the correlation coefficient of the time domain basis C based on the magnetic field measurement data B and the time domain basis Cout based on the external space data ^Bout, by a method or the like based on the principal component analysis. For example, the calculation processing section 1170 performs the singular value decomposition on the covariance of the time domain basis C based on the magnetic field measurement data B and the time domain basis Cout based on the external space data ^Bout, and calculates the coefficient of the correlation by the magnitude of the singular value. Such a correlation coefficient for a portion corresponding to the time change common to the basis C and the basis Cout is close to 1 (a strong correlation), and random noise or the like is close to 0 (decorrelation).

In step 1340, the magnetic field measurement device 10 extracts, as an intersection P, the variation component common to the time domain basis C based on the magnetic field measurement data B and the time domain basis Cout based on the external space data ^Bout. For example, the calculation processing section 1170 regards and extracts, as an intersection, a portion in which the coefficient of the correlation exceeds a predetermined threshold value L. In this way, the calculation processing section 1170 extracts the common variation component based on the strength of the correlation between the time domain basis C based on the magnetic field measurement data B and the time domain basis Cout based on the external space data ^Bout. It should be noted that when the threshold value L is set too high, the disturbance cannot be removed, and when the threshold value L is set too low, even the magnetocardiographic signal which is the measurement target is removed, and thus it is preferable to set the threshold value L to an appropriate value.

$$P = C \cap C_{OUT} \quad \text{[Math. 16]}$$

In this way, the calculation processing section 1170 extracts the common variation component by performing the principal component analysis on the time domain basis C based on the magnetic field measurement data B and the time domain basis Cout based on the external space data ^Bout. However, the present invention is not limited to this. Instead of the principal component analysis, the calculation processing section 1170 may extract the common variation component, for example, by different methods such as independent component analysis.

In step 1350, the magnetic field measurement device 10 removes the common variation component from the internal space data ^Bin. For example, the calculation processing section 1170 removes, from the internal space data ^Bin, at least a part of the variation component common to the magnetic field measurement data B that indicates the spatial distribution of the magnetic field which is indicated by the measurement data, and the external space data ^Bout. More specifically, the calculation processing section 1170 removes the common variation component by the following Expression. That is, the calculation processing section 1170 uses a method of SSP (Signal Space Projection) to remove the intersection P from the internal space data ^Bin by the calculation. It should be noted that in the following Expression, tSSS is an abbreviation for spatio-Temporal Signal Space Separation, and ^Bin_tSSS represents the internal space data after the common variation component is removed by this flow.

$$\hat{B}_{in\_tSSS} = [(I-PP^T)\hat{B}^T_{in}]^T \qquad \text{[Math.17]}$$

Figure 14:
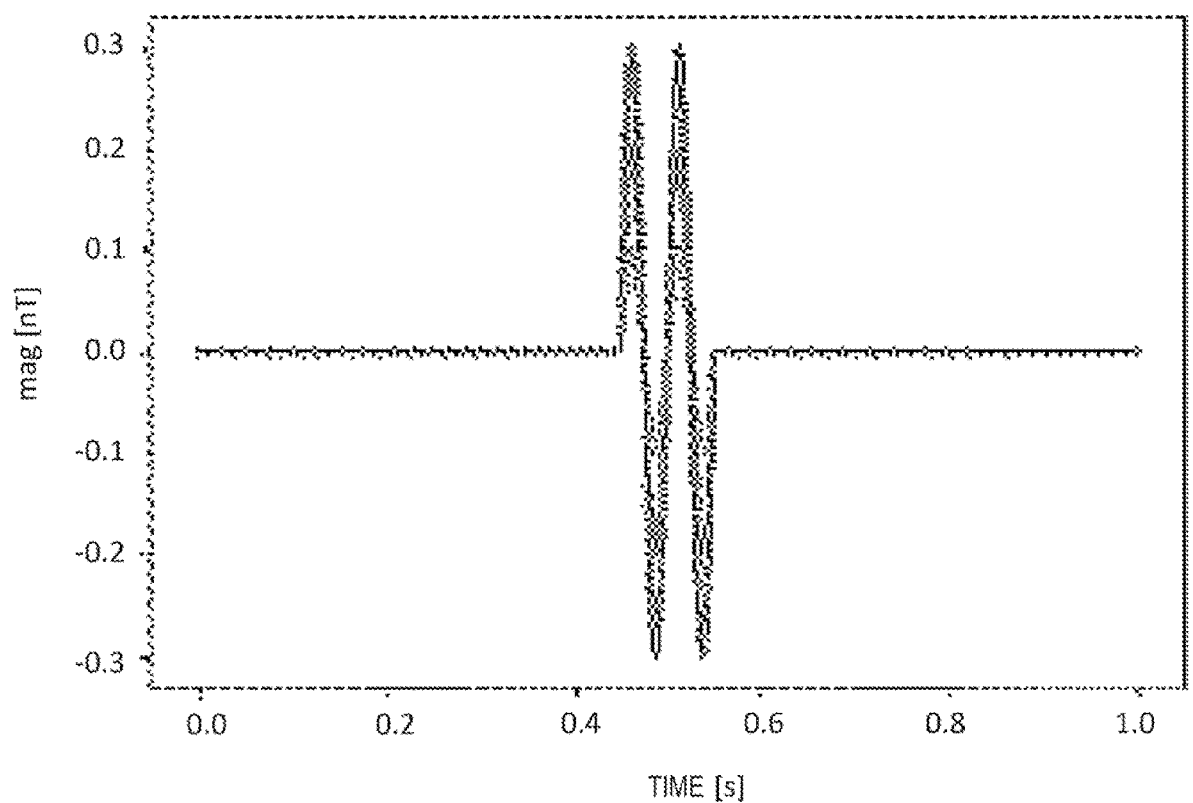
FIG. 14 shows a simulation result of magnetic field measurement data B according to the present embodiment.

FIG. 14 shows a simulation result of magnetic field measurement data B according to the present embodiment. In carrying out the present simulation, as the magnetic sensor array 210, the magnetic sensor array 210, which is configured by 8×8×2=128 magnetic sensor cells 220 being three-dimensionally arrayed to form the surface covering at least a part of the measurement target as shown in FIG. 9, is used. Further, an interference magnetic field of Bx=100 pT, By=200 pT, and Bz=300 pT is input to the magnetic sensor array 210 from an infinite distance that makes an completely external space. In the present drawing, the horizontal axis shows the time and the vertical axis shows the magnitude of magnetic field measurement data.

Figure 15:
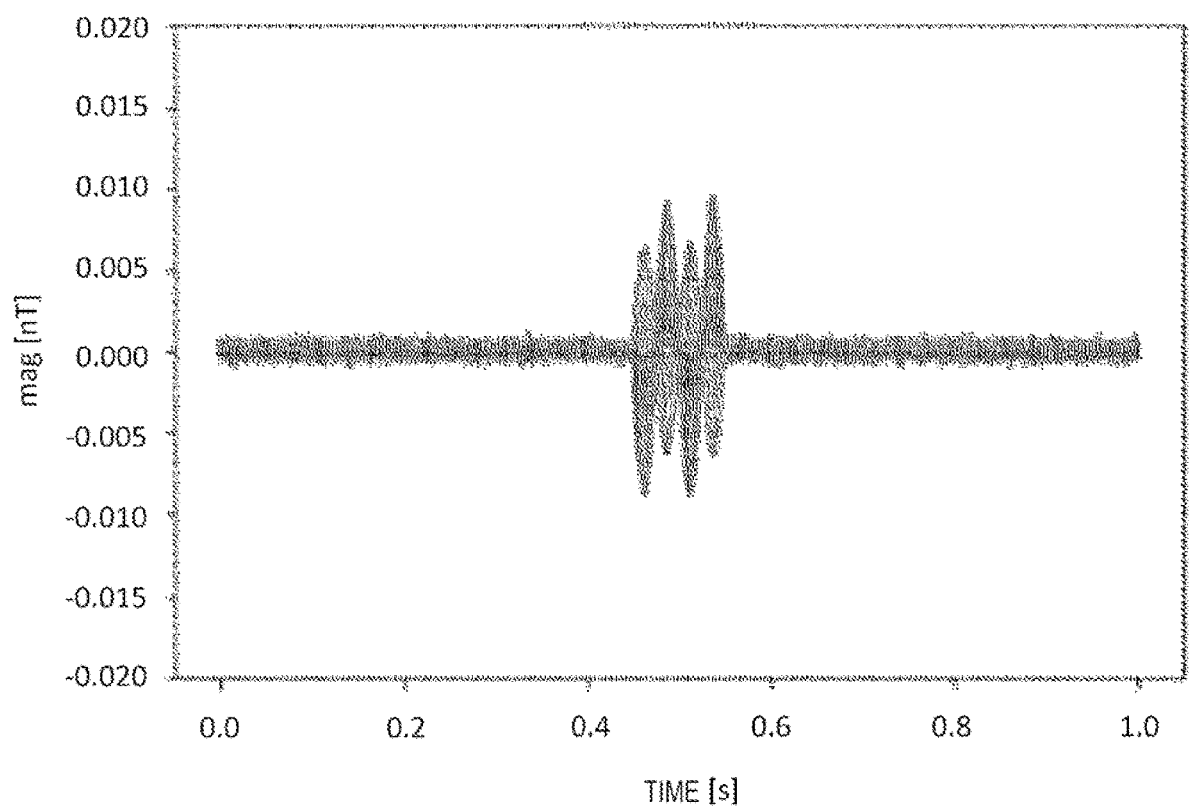
FIG. 15 shows a simulation result of the internal space data ^Bin before removal of a common variation component according to the present embodiment.

FIG. 15 shows a simulation result of the internal space data ^Bin before removal of a common variation component according to the present embodiment. In carrying out the present simulation, the signal space separation is performed under the conditions that the sensor error ϑ=1%, and Lin=6 and Lout=3. In the present drawing, the horizontal axis represents the time, and the vertical axis represents the magnitude of the internal space data ^Bin before the removal of the common variation component. As shown in the present drawing, it can be seen that the interference magnetic field input from the external space remains in the internal space data ^Bin. Such an interference magnetic field increases in proportion to the magnitude of the sensor error E.

Figure 16:
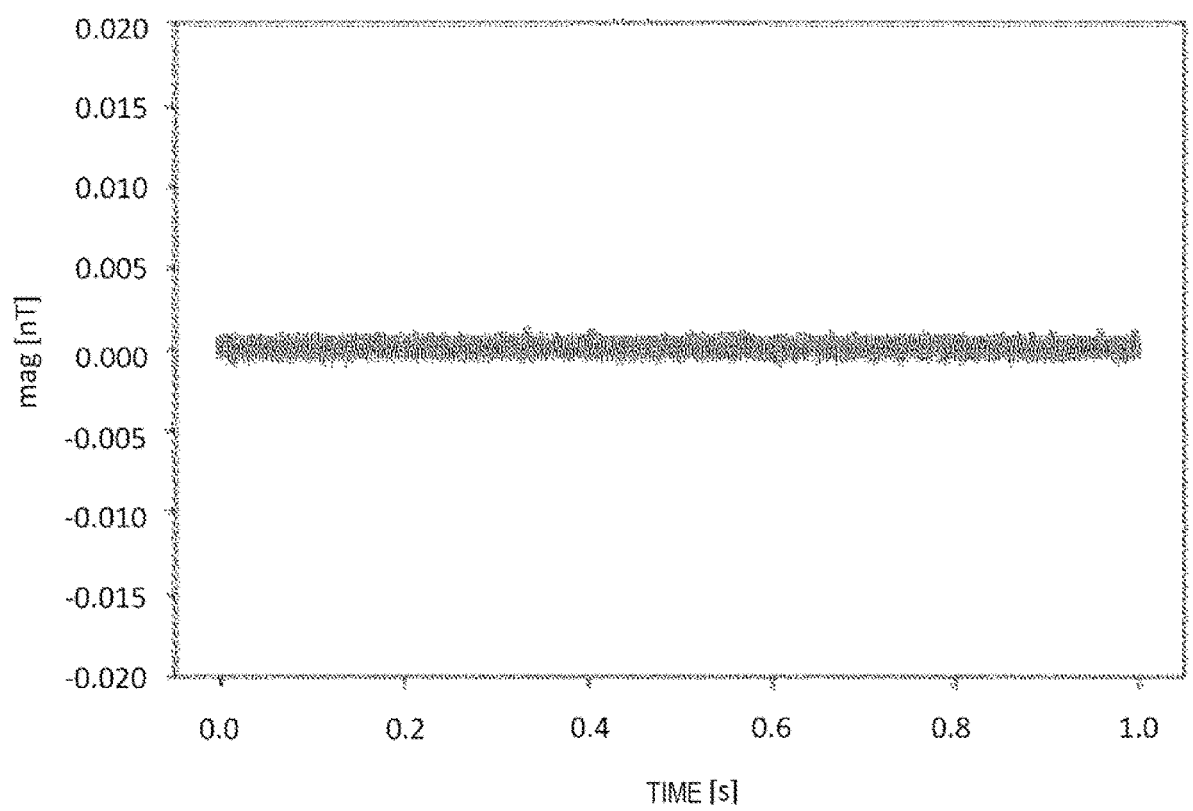
FIG. 16 shows a simulation result of internal space data ^Bin_tSSS after removal of the common variation component according to the present embodiment.

FIG. 16 shows a simulation result of internal space data ^Bin_tSSS after removal of the common variation component according to the present embodiment. In carrying out the present simulation, the common variation component is removed from the internal space data ^Bin by tSSS with the threshold value L=0.99 in the time range of 0s to 1s. It should be noted that the sensor error ϑ is set to 1%, similarly to that of the simulation in FIG. 15. In the present drawing, the horizontal axis represents the time, and the vertical axis represents the magnitude of the internal space data ^Bin_tSSS after the removal of the common variation component. As shown in the present drawing, it can be seen that the interference magnetic field, from the external space, remaining due to the sensor error can be removed by tSSS.

As described above, in carrying out the signal space separation processing, when the magnetic sensor has the sensor error in sensitivity or position, a disturbance removal performance deteriorates, and even the interference magnetic field from the external space cannot be separated accurately and may remain. Further, in the case where the magnetic sensor has the magnetic resistance element, and further in the case where the magnetic sensor has the magnetic flux concentrator, such remaining of interference magnetic field may be more prominent due to an increase in sensor error based on a manufacturing error or an implementation error of those. In contrast, the magnetic field measurement device 10 according to the present embodiment removes, from the internal space data ^Bin, at least a part of the variation component common to the magnetic field measurement data B and the external space data ^Bout. Thereby, with the magnetic field measurement device 10 according to the present embodiment, it is possible to improve the disturbance removal performance, and to remove the interference magnetic field remaining due to the sensor error, more accurately. Here, in extracting the common variation component, it is conceivable to compare the internal space data ^Bin with the external space data ^Bout to extract the variation component common to both. However, in this case, although the intermediate space magnetic field Bintermediate can be extracted almost accurately, the external space magnetic field Bout cannot be accurately extracted because the sensor error ϑ is small. In contrast, with the magnetic field measurement device 10 according to the present embodiment, the magnetic field measurement data B before the signal space separation is performed, rather than the internal space data ^Bin, is compared with the external space data ^Bout to extract the common variation component, and thus it is also possible to accurately extract the external space magnetic field Bout in addition to the intermediate space magnetic field Bintermediate. Accordingly, with the magnetic field measurement device 10 according to the present embodiment, it is possible to more improve the disturbance removal performance of the interference magnetic field.

Here, in the above description, the case where the magnetic field measurement device 10 removes, from the internal space data ^Bin, at least a part of the variation component common to the magnetic field measurement data B and the external space data ^Bout is shown as one example. However, the present invention is not limited to this. In the magnetic field measurement device 10 according to the modification example, the calculation processing section 1170 may remove, from the internal space data ^Bin, at least a part of the variation component common to data obtained by subtracting the internal space data ^Bin from the magnetic field measurement data B, and the external space data ^Bout. That is, the calculation processing section 1170 may extract, as the intersection P, the variation component common to the time domain basis C based on the data obtained by subtracting the internal space data ^Bin from the magnetic field measurement data B, and the time domain basis Cout based on the external space data ^Bout. Further, the calculation processing section 1170 may manually remove, from the internal space data ^Bin by the calculation, the intersection P extracted in this way by using, for example, the method of SSP.

It should be noted that the magnetic field measurement device 10 according to the present embodiment can simultaneously perform the actual measurement of the magnetic field to be measured, and the SSS processing and the tSSS processing. That is, the magnetic field measurement device 10 according to the present embodiment can simultaneously perform the magnetocardiographic measurement, the SSS processing, and the tSSS processing, in a state in which the magnetic sensor array 210 is arranged such that the heart of the subject to be measured, which is the measurement target, exists in the internal space. Thereby, with the magnetic field measurement device 10 according to the present embodiment, it is not necessary to perform the SSS processing and the tSSS processing at a timing different from that of the magnetocardiographic measurement, and it is possible to simplify the process. However, the present invention is not limited to this. The magnetic field measurement device 10 according to the present embodiment may perform the SSS processing and tSSS processing, in advance in a state in which the heart of the subject to be measured, which is the measurement target, does not exist in the internal space, and then perform the magnetocardiographic measurement by arranging the magnetic sensor array 210 such that the heart of the subject to be measured, which is the measurement target, exists in the internal space, and remove the common variation component by the SSP processing.

Various embodiments of the present invention may be described with reference to flowcharts and block diagrams whose blocks may represent (1) steps of processes in which operations are performed or (2) sections of apparatuses responsible for performing operations. Certain steps and "sections" may be implemented by dedicated circuitry, programmable circuitry supplied with computer-readable instructions stored on computer-readable media, and/or processors supplied with computer-readable instructions stored on computer-readable media. Dedicated circuitry may include digital and/or analog hardware circuits and may include integrated circuits (IC) and/or discrete circuits. Programmable circuitry may include reconfigurable hardware circuits comprising logical AND, OR, XOR, NAND, NOR, and other logical operations, flip-flops, registers, memory elements, etc., such as field-programmable gate arrays (FPGA), programmable logic arrays (PLA), and the like.

A computer-readable medium may include any tangible device that can store instructions to be executed by a suitable device, and as a result, the computer-readable medium having instructions stored in the tangible device comprises an article of manufacture including instructions which can be executed to create means for executing operations specified in the flowcharts or block diagrams. Examples of the computer-readable medium may include an electronic storage medium, a magnetic storage medium, an optical storage medium, an electromagnetic storage medium, a semiconductor storage medium, etc. More specific examples of the computer-readable medium may include a floppy (registered trademark) disk, a diskette, a hard disk, a random access memory (RAM), a read-only memory (ROM), an erasable programmable read-only memory (EPROM or Flash memory), an electrically erasable programmable read-only memory (EEPROM), a static random access memory (SRAM), a compact disc read-only memory (CD-ROM), a digital versatile disk (DVD), a Blu-ray (registered trademark) disc, a memory stick, an integrated circuit card, etc.

Computer-readable instructions may include assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk (registered trademark), JAVA (registered trademark), C++, etc., and conventional procedural programming languages, such as the "C" programming language or similar programming languages.

Computer-readable instructions may be provided to a processor of a general-purpose computer, special purpose computer, or other programmable data processing apparatus, or to programmable circuitry, locally or via a local area network (LAN), wide area network (WAN) such as the Internet, etc., so that the computer-readable instructions are executed to create means for performing operations specified in the flowcharts or block diagrams. Examples of processors include computer processors, processing units, microprocessors, digital signal processors, controllers, microcontrollers, etc.

Figure 17:
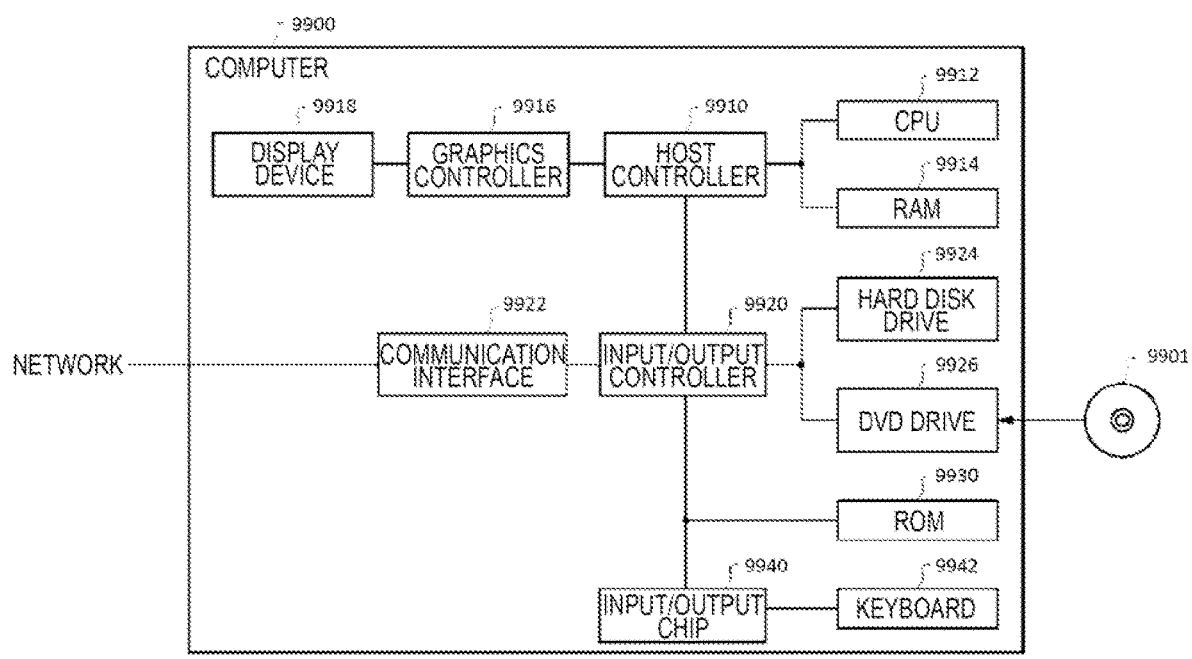
FIG. 17 shows an example of a computer 9900 in which a plurality of aspects of the present invention may be embodied entirely or partially.

FIG. 17 shows an example of a computer 9900 in which a plurality of aspects of the present invention may be embodied entirely or partially. A program that is installed in the computer 9900 can cause the computer 9900 to function as operations associated with apparatuses according to the embodiments of the present invention or one or more sections of the apparatuses, or can cause the computer 9900 to execute the operations or the one or more sections thereof, and/or can cause the computer 9900 to execute processes according to the embodiments of the present invention or steps of the processes. Such a program may be performed by a CPU 9912 so as to cause the computer 9900 to perform certain operations associated with some or all of the blocks of flowcharts and block diagrams described herein.

The computer 9900 according to the present embodiment includes the CPU 9912, a RAM 9914, a graphics controller 9916, and a display device 9918, which are mutually connected by a host controller 9910. The computer 9900 also includes input/output units such as a communication interface 9922, a hard disk drive 9924, a DVD-ROM drive 9926, and an IC card drive, which are connected to the host controller 9910 via an input/output controller 9920. The computer also includes legacy input/output units such as a ROM 9930 and a keyboard 9942, which are connected to the input/output controller 9920 via an input/output chip 9940.

The CPU 9912 operates according to programs stored in the ROM 9930 and the RAM 9914, thereby controlling each unit. The graphics controller 9916 acquires image data generated by the CPU 9912 on a frame buffer or the like provided in the RAM 9914 or in itself, and causes the image data to be displayed on the display device 9918.

The communication interface 9922 performs communication with other electronic devices via a network. The hard disk drive 9924 stores programs and data that are used by the CPU 9912 within the computer 9900. The DVD-ROM drive 9926 reads the programs or the data from the DVD-ROM 9901, and provides the hard disk drive 9924 with the programs or the data via the RAM 9914. The IC card drive reads programs and data from an IC card, and/or writes programs and data into the IC card.

The ROM 9930 stores therein a boot program or the like that is performed by the computer 9900 at the time of activation, and/or a program depending on the hardware of the computer 9900. The input/output chip 9940 may also connect various input/output units to the input/output controller 9920 via a parallel port, a serial port, a keyboard port, a mouse port, or the like.

A program is provided by computer-readable media such as the DVD-ROM 9901 or the IC card. The program is read from the computer-readable media, installed into the hard disk drive 9924, RAM 9914, or ROM 9930, which are also examples of the computer-readable media, and performed by the CPU 9912. Information processing written in these programs is read by the computer 9900, resulting in cooperation between a program and the above-mentioned various types of hardware resources. An apparatus or method may be constituted by realizing the operation or processing of information in accordance with the usage of the computer 9900.

For example, when communication is performed between the computer 9900 and an external device, the CPU 9912 may perform a communication program loaded onto the RAM 9914 to instruct communication processing to the communication interface 9922, based on the processing written in the communication program. The communication interface 9922, under control of the CPU 9912, reads transmission data stored on a transmission buffer region provided in a recording medium such as the RAM 9914, the hard disk drive 9924, the DVD-ROM 9901, or the IC card, and transmits the read transmission data to a network or writes reception data received from a network into a reception buffer region or the like provided on the recording medium.

In addition, the CPU 9912 may cause all or a necessary portion of a file or a database to be read into the RAM 9914, the file or the database having been stored in an external recording medium such as the hard disk drive 9924, the DVD-ROM drive 9926 (DVD-ROM 9901), the IC card, etc., and perform various types of processing on the data on the RAM 9914. The CPU 9912 then writes back the processed data to the external recording medium.

Various types of information, such as various types of programs, data, tables, and databases, may be stored in the recording medium to undergo information processing. The CPU 9912 may execute various types of processing on the data read from the RAM 9914 to write back a result to the RAM 9914, the processing being described throughout the present disclosure, specified by an instruction sequence of the programs, and including various types of operations, information processing, condition determinations, conditional branch, unconditional branch, information retrievals/replacements, or the like. In addition, the CPU 9912 may search for information in a file, a database, etc., in the recording medium. For example, when a plurality of entries, each having an attribute value of a first attribute associated with an attribute value of a second attribute, are stored in the recording medium, the CPU 9912 may search for an entry matching the condition whose attribute value of the first attribute is designated, from among the plurality of entries, and read the attribute value of the second attribute stored in the entry, thereby obtaining the attribute value of the second attribute associated with the first attribute satisfying the predetermined condition.

The above-described program or software modules may be stored in the computer-readable medium on the computer 9900 or near the computer 9900. In addition, a recording medium such as a hard disk or a RAM provided in a server system connected to a dedicated communication network or the Internet can be used as the computer-readable medium, thereby providing the program to the computer 9900 via the network.

While the embodiments of the present invention have been described, the technical scope of the invention is not limited to the above-described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10 magnetic field measurement device; 100 main body section; 110 magnetic sensor unit; 120 head; 125 drive section; 130 base section; 140 pole section; 150 information processing section; 210 magnetic sensor array; 220 magnetic sensor cell; 230 sensor data collection section; 300 sensor section; 520 magnetic sensor; 530 magnetic field generation section; 532 amplifier circuit; 534 coil; 540 output section; 702 magnetic resistance element; 704, 706 magnetic flux concentrator; 1100 sensor data processing section; 1110 AD converter; 1112 clock generator; 1120 magnetic field acquisition section; 1130 calibration calculation section; 1140 data output section; 1150 basis vector storage section; 1160 signal space separation section; 1170 calculation processing section; 9900 computer; 9901 DVD-ROM; 9910 host controller; 9912 CPU; 9914 RAM; 9916 graphics controller; 9918 display device; 9920 input/output controller; 9922 communication interface; 9924 hard disk drive; 9926 DVD-ROM drive; 9930 ROM; 9940 input/output chip; 9942 keyboard

What is claimed is:

1. A magnetic field measurement device that measures bio-magnetic fields of a living subject, comprising:
    a magnetic sensor array configured by a plurality of magnetic sensor cells, each of which has a magnetic sensor;
    at least one processor;
    a magnetic field acquisition section configured to acquire measurement data measured by the magnetic sensor array; a signal space separation section configured to perform signal separation to separate, into internal space data and external space data, a spatial distribution of a magnetic field which is indicated by the measurement data, based on a position and a magnetic sensitivity of each magnetic sensor; and
    a calculation processing section configured to remove, using the at least one processor, from the internal space data, at least a part of a variation component common to magnetic field measurement data that indicates the spatial distribution of the magnetic field which is indicated by the measurement data, and the external space data.

2. The magnetic field measurement device according to claim 1, wherein
    the calculation processing section is configured to extract, using the at least one processor, the common variation component based on a correlation between a time domain basis based on the magnetic field measurement data, and a time domain basis based on the external space data.

3. The magnetic field measurement device according to claim 2, wherein
    the calculation processing section is configured to respectively calculate, using the at least one processor, the time domain basis based on the magnetic field measurement data and the time domain basis based on the external space data, by respectively performing singular value decomposition on the magnetic field measurement data and the external space data.

4. The magnetic field measurement device according to claim 2, wherein
    the calculation processing section is configured to extract, using the at least one processor, the common variation component by performing principal component analysis on the time domain basis based on the magnetic field measurement data and the time domain basis based on the external space data.

5. The magnetic field measurement device according to claim 4, wherein
    the calculation processing section is configured to calculate, using the at least one processor, a coefficient of the correlation by performing singular value decomposition on a covariance of the time domain basis based on the magnetic field measurement data and the time domain basis based on the external space data, and extract, as the common variation component, a component of which the coefficient of the correlation exceeds a predetermined threshold value.

6. The magnetic field measurement device according to claim 5, wherein
the magnetic sensor includes a magnetic resistance element.

7. The magnetic field measurement device according to claim 6, wherein
the magnetic sensor further includes magnetic flux concentrators that are respectively arranged at both of one end and another end of the magnetic resistance element.

8. The magnetic field measurement device according to claim 1, wherein
each of the plurality of magnetic sensor cells further includes
a magnetic field generation section configured to generate a feedback magnetic field to reduce an input magnetic field detected by the magnetic sensor, and
an output section configured to output an output signal in accordance with a feedback current which is caused to flow for the magnetic field generation section to generate the feedback magnetic field.

9. The magnetic field measurement device according to claim 2, wherein
each of the plurality of magnetic sensor cells further includes
a magnetic field generation section configured to generate a feedback magnetic field to reduce an input magnetic field detected by the magnetic sensor, and
an output section configured to output an output signal in accordance with a feedback current which is caused to flow for the magnetic field generation section to generate the feedback magnetic field.

10. The magnetic field measurement device according to claim 1, wherein
the signal space separation section is configured to perform the signal separation on the spatial distribution of the magnetic field, based on basis vectors calculated from orthonormal functions, and the position and the magnetic sensitivity.

11. The magnetic field measurement device according to claim 10, wherein
the signal space separation section is configured to perform the signal separation on the spatial distribution of the magnetic field, through series expansion of the basis vectors.

12. The magnetic field measurement device according to claim 11, wherein
the signal space separation section is configured to calculate expansion coefficients of the basis vectors by a method of least squares.

13. The magnetic field measurement device according to claim 10, wherein
the orthonormal functions are expressed with spherical harmonics.

14. The magnetic field measurement device according to claim 1, further comprising:
a calibration calculation section configured to calibrate, using the at least one processor, the measurement data acquired by the magnetic field acquisition section.

15. The magnetic field measurement device according to claim 1, wherein
the magnetic sensor array is configured by the plurality of magnetic sensor cells being arrayed to form a surface covering at least a part of a measurement target.

16. The magnetic field measurement device according to claim 15, wherein
in the magnetic sensor array, the plurality of magnetic sensor cells are three-dimensionally arrayed to be arranged at grid points between two curved surfaces curved in one direction.

17. The magnetic field measurement device according to claim 16, wherein
the curved surfaces are formed to be substantially parabolic.

18. The magnetic field measurement device according to claim 1, wherein
the calculation processing section is configured to remove, using the at least one processor, from the internal space data, at least a part of a variation component common to data obtained by subtracting the internal space data from the magnetic field measurement data, and the external space data.

19. A magnetic field measurement method that measures bio-magnetic fields of a living subject, comprising:
acquiring measurement data measured by a magnetic sensor array configured by a plurality of magnetic sensor cells, each of which has a magnetic sensor;
performing signal separation to separate, into internal space data and external space data, a spatial distribution of a magnetic field which is indicated by the measurement data, based on a position and a magnetic sensitivity of each magnetic sensor; and
removing from the internal space data, at least a part of a variation component common to magnetic field measurement data that indicates the spatial distribution of the magnetic field which is indicated by the measurement data, and the external space data.

20. A non-transitory recording medium having recorded thereon a magnetic field measurement program that measures bio-magnetic fields of a living subject and is executed by a computer and that causes the computer to function as:
a magnetic field acquisition section configured to acquire measurement data measured by a magnetic sensor array configured by a plurality of magnetic sensor cells, each of which has a magnetic sensor;
a signal space separation section configured to perform signal separation to separate, into internal space data and external space data, a spatial distribution of a magnetic field which is indicated by the measurement data, based on a position and a magnetic sensitivity of each magnetic sensor; and
a calculation processing section configured to remove using at least one processor, from the internal space data, at least a part of a variation component common to magnetic field measurement data that indicates the spatial distribution of the magnetic field which is indicated by the measurement data, and the external space data.

* * * * *